United States Patent
McKenna et al.

(10) Patent No.: US 9,615,781 B2
(45) Date of Patent: Apr. 11, 2017

(54) SYSTEMS AND METHODS FOR MONITORING DEPTH OF CONSCIOUSNESS

(75) Inventors: Edward M. McKenna, Boulder, CO (US); Bo Chen, Louisville, CO (US); Youzhi Li, Longmont, CO (US); Paul Stanley Addison, Edinburgh (GB); James N. Watson, Dunfermline (GB)

(73) Assignee: COVIDIEN LP, Mansfield, MA (US)

(*) Notice: Subject to any disclaimer, the term of this patent is extended or adjusted under 35 U.S.C. 154(b) by 1234 days.

(21) Appl. No.: 13/364,766

(22) Filed: Feb. 2, 2012

(65) Prior Publication Data

US 2012/0203087 A1 Aug. 9, 2012

Related U.S. Application Data

(60) Provisional application No. 61/439,281, filed on Feb. 3, 2011.

(51) Int. Cl.
*A61B 5/00* (2006.01)
*G06F 19/00* (2011.01)
*A61B 5/1455* (2006.01)
*A61B 5/04* (2006.01)
*A61B 5/0476* (2006.01)

(52) U.S. Cl.
CPC ...... *A61B 5/14551* (2013.01); *A61B 5/04001* (2013.01); *A61B 5/0476* (2013.01); *A61B 5/40* (2013.01); *A61B 5/4821* (2013.01); *G06F 19/345* (2013.01); *G06F 19/3431* (2013.01); *A61B 5/7239* (2013.01); *A61B 5/7264* (2013.01)

(58) Field of Classification Search
CPC ... A61B 5/1455; A61B 5/0476; A61B 5/4821; A61B 5/02028; A61B 5/02; A61B 5/072; A61B 5/4848; A61B 5/4058; G06F 19/34; G06F 19/3431
See application file for complete search history.

(56) References Cited

U.S. PATENT DOCUMENTS

| | | | |
|---|---|---|---|
| 4,907,597 A | 3/1990 | Chamoun | |
| 6,338,713 B1 | 1/2002 | Chamoun et al. | |
| 7,367,949 B2 | 5/2008 | Korhonen et al. | |
| 7,407,485 B2 | 8/2008 | Huiku | |
| 7,407,486 B2 | 8/2008 | Huiku | |
| 8,216,136 B2 | 7/2012 | Addison et al. | |

(Continued)

*Primary Examiner* — William Thomson
*Assistant Examiner* — Marie Archer

(57) ABSTRACT

During patient monitoring, a depth of consciousness (DOC) measure, such as a bispectral index, may be used in conjunction with additional information obtained from an awareness metric derived from one or more physiological signals, such as a photoplethysmograph signal. In an embodiment, a DOC measure may be combined with information from an awareness metric to produce a combined DOC measure. In an embodiment, information from an awareness metric derived from one or more physiological signals may be used to provide an indication of confidence in a DOC measure. In an embodiment, a DOC measure may be used to provide an indication of confidence in a depth of consciousness assessment based on an awareness metric. In an embodiment, one or the other of a DOC measure and an awareness metric may be used to provide an indication of a patient's depth of consciousness (e.g., by one "overriding" the other).

20 Claims, 12 Drawing Sheets

(56) References Cited

U.S. PATENT DOCUMENTS

| | | |
|---|---|---|
| 8,290,730 B2 | 10/2012 | Watson et al. |
| 2004/0193068 A1* | 9/2004 | Burton ................. A61B 5/0476 600/544 |
| 2006/0217628 A1 | 9/2006 | Huiku |
| 2007/0167694 A1 | 7/2007 | Causevic et al. |
| 2008/0167540 A1 | 7/2008 | Korhonen et al. |
| 2008/0188760 A1* | 8/2008 | Al-Ali et al. ................. 600/507 |
| 2009/0275853 A1* | 11/2009 | Sarkela .............. A61B 5/04014 600/544 |
| 2009/0326393 A1 | 12/2009 | Sethi |
| 2009/0326395 A1 | 12/2009 | Watson |
| 2009/0326402 A1 | 12/2009 | Addison et al. |
| 2010/0013642 A1 | 1/2010 | Addison et al. |
| 2011/0137297 A1* | 6/2011 | Kiani et al. ................. 604/890.1 |
| 2011/0270047 A1* | 11/2011 | O'Brien ........................ 600/301 |

* cited by examiner

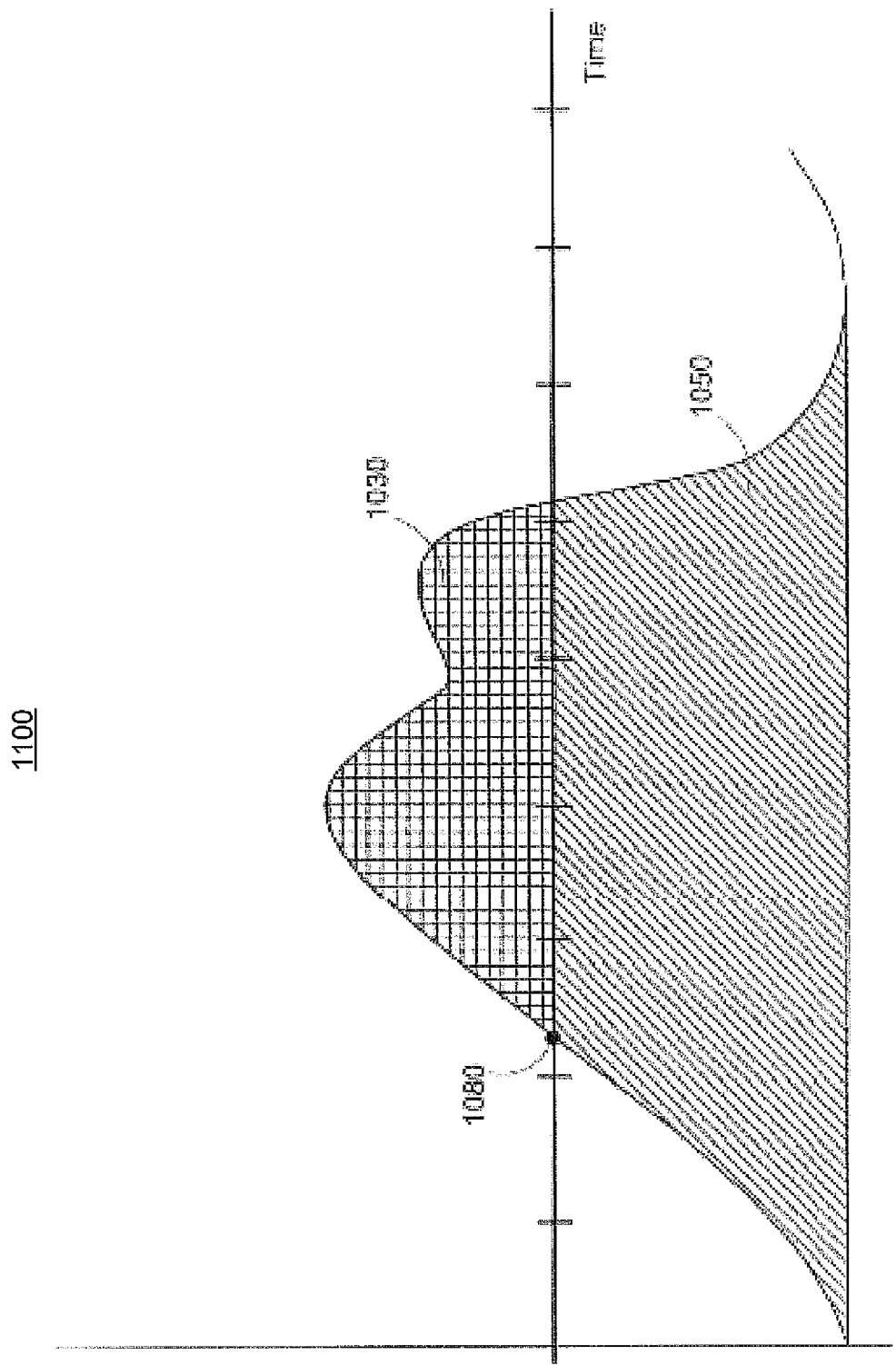

SYSTEMS AND METHODS FOR MONITORING DEPTH OF CONSCIOUSNESS

This application claims the benefit of U.S. Provisional Application No. 61/439,281, filed Feb. 3, 2011, 2008, which is hereby incorporated by reference herein in its entirety.

SUMMARY

This disclosure relates to assessing the depth of consciousness of a subject and, more particularly, this disclosure relates to assessing depth of consciousness using a physiological signal, such as a photoplethysmograph signal, in conjunction with a depth of consciousness measure, such as a bispectral index.

Some techniques for monitoring depth of consciousness utilize a patient's electrophysiological signals, such as electroencephalogram (EEG) signals, electromyogram (EMG) signals, and/or electrooculogram (EOG) signals. Such techniques may process one or more of these signals to supply a consciousness index, indicating a patient's depth of consciousness (DOC) on a scale. For example, the bispectral (BIS) index is a processed parameter which may be derived utilizing a composite of measures from EEG and physiological signal processing techniques including bispectral analysis, power spectral analysis, and time domain analysis. The BIS algorithm may be based at least in part on EEG signal features (bispectral and others) which may be highly correlated with sedation/hypnosis, including the degree of high frequency (14 to 30 Hz) activation, the amount of low frequency synchronization, the presence of nearly suppressed periods within the EEG, and the presence of fully suppressed (i.e., isoelectric, "flat line") periods within an EEG. The BIS index may provide an indication of a subject's DOC, with an index value of 0 representing a "flat line" EEG and an index value of 100 indicating a fully awake subject. Such a DOC measure may be used by care providers in operating room or intensive care settings to evaluate a patient's status and provide treatment accordingly (e.g., adjusting anesthetic or analgesic administration).

For example, a BIS value of 60 may have a high sensitivity for identifying drug-induced unconsciousness. However, in some settings and with some combinations of sedatives and analgesics, unconscious individuals may have BIS values greater than 60. Factors other than drug administration that can influence brain metabolism (e.g., alterations in temperature or physiologic homeostasis) may also produce changes in the BIS index. Additionally, the sudden appearance of a low BIS value may indicate the onset of a serious clinical condition.

BIS values may also be influenced by a range of additional factors. Potential artifacts may be caused by poor contact (high impedance) between the sensor and the subject's skin, muscle activity or rigidity, head and body motion, sustained eye movements, improper sensor placement and unusual or excessive electrical interference. EMG artifact or residual neuro-muscular blocker (NMB) effects may lead to high BIS values in an unresponsive patient. Further, a BIS value may not be instantaneously altered by changes in clinical status. When abrupt changes occur in hypnotic state—for example, during induction or rapid emergence—the BIS value may lag behind the observed clinical change by approximately 5 to 10 seconds.

These complicating factors in the interpretation of BIS values have led some clinicians to utilize BIS monitors alongside standard techniques such as patient observation and conventional patient monitors (e.g., devices that track a patient's pulse and blood pressure). However, simply using multiple modalities may not improve a care provider's understanding of a patient's depth of consciousness. Patient awareness may occur even when conventional vital signs are normal, and standard techniques may fail to detect consciousness when a patient has been administered a muscle relaxant or medication (e.g., beta blockers). Moreover, the range of BIS values which indicates an appropriate depth of consciousness may be influenced by a number of patient conditions. For example, certain conditions have been associated with low BIS values during the intraoperative period, presumably because of marked reduction in cerebral metabolism, including cardiac arrest, hypovolemia, hypotension, cerebral ischemia, hypoperfusion, hypoglycemia, hypothermia and anoxia.

Additional physiological signals may contain information about a patient's depth of consciousness. For example, a photoplethysmograph (PPG) signal may exhibit one or more waveform features which indicate consciousness. For example, a change in an augmentation index or a baseline value may indicate a change in patient awareness, as discussed in additional detail below. Rather than simply utilizing multiple monitors in a treatment setting, depth of consciousness monitoring may be improved by combining information arising from additional physiological signals, such as a PPG signal, with a DOC measure such as a BIS index. During patient monitoring, a DOC measure, such as the BIS index, may be used in conjunction with information obtained from an awareness metric derived from one or more physiological signals. In an embodiment, a DOC measure may be combined with information from an awareness metric derived from one or more physiological signals to produce a combined DOC measure. In an embodiment, information from an awareness metric derived from one or more physiological signals may be used to provide an indication of confidence in a DOC measure. In an embodiment, a DOC measure may be used to provide an indication of confidence in a depth of consciousness assessment based on an awareness metric derived from a physiological signal. In an embodiment, one or the other of a DOC measure and an awareness metric derived from a physiological signal may be used to provide an indication of a patient's depth of consciousness (e.g., by one "overriding" the other).

BRIEF DESCRIPTION OF THE DRAWINGS

The above and other features of the present invention, its nature and various advantages will be more apparent upon consideration of the following detailed description, taken in conjunction with the accompanying drawings in which.

DETAILED DESCRIPTION

This disclosure generally relates to depth of consciousness assessment based on physiological signals. These physiological signals may be received by an appropriate sensing device, and may be analog or digital. For illustrative purposes, portions of this disclosure will be described in the context of a time-domain electrophysiological signal (sensed, for example, by one or more electrodes) and a photoplethysmograph (PPG) signal (generated, for example, by one or more components of a pulse oximetry system). It will be understood that any physiological signals, such as an electrophysiological signal or a PPG signal, may be generated by any suitable device(s) capable of generating such signals. It will also be understood that the present disclosure is applicable to any suitable signals and that electrophysiological signals and PPG signals are used merely for illustrative purposes. Those skilled in the art will recognize that the present disclosure has wide applicability to other signals including, but not limited to, other biosignals (e.g., electrocardiogram, electroencephalogram, electrogastrogram, electromyogram, electrooculogram, heart rate signals, accelerometer signals, respiration monitor signals, pathological sounds, ultrasound, any other suitable biosignal) or combinations thereof.

Figure 1:
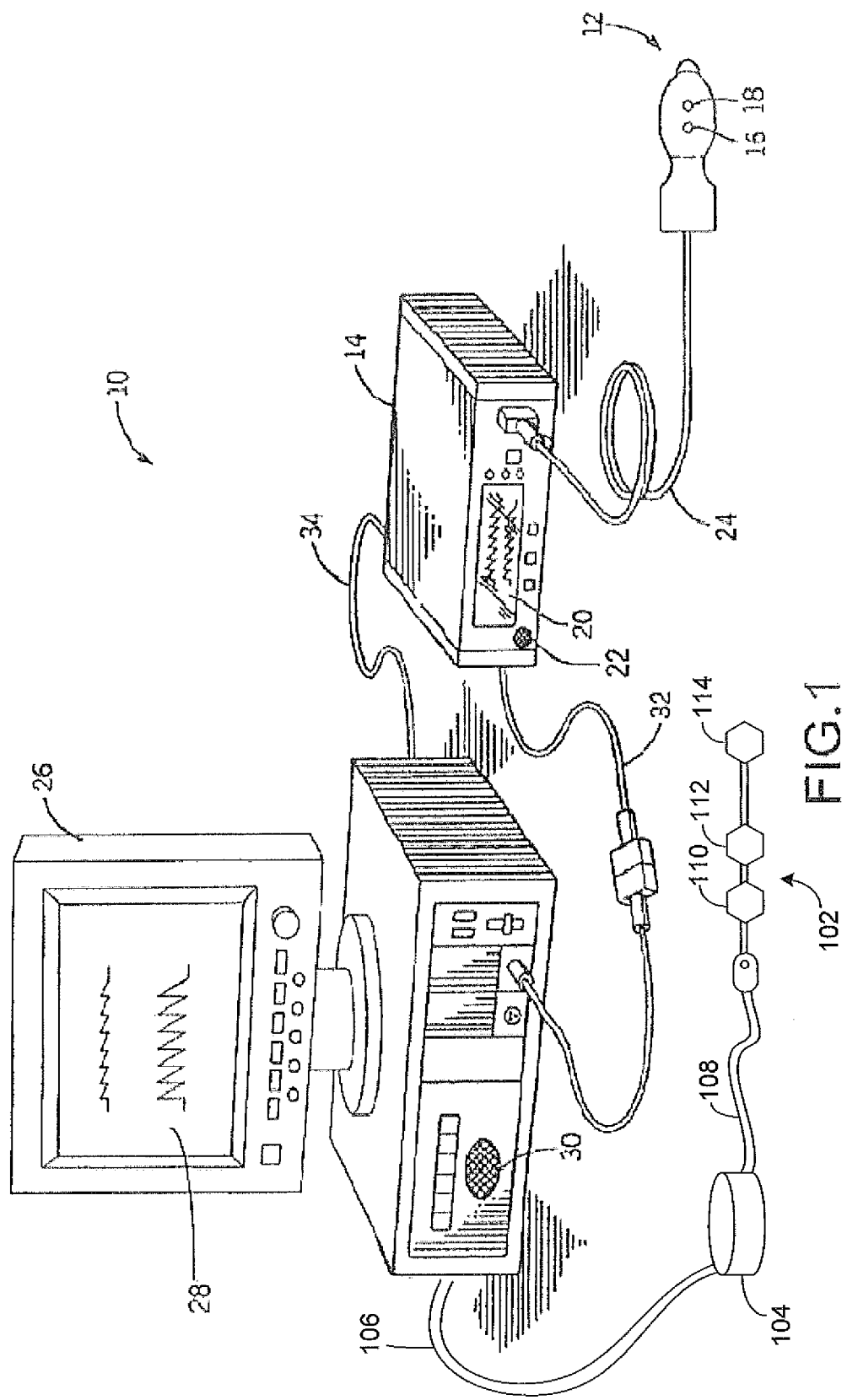
FIG. 1 shows an illustrative patient monitoring system in accordance with an embodiment.

FIG. 1 is a perspective view of an embodiment of patient monitoring system 10. In an embodiment, system 10 may be implemented as part of a pulse oximetry system. In an embodiment, system 10 may be implemented as part of a depth of consciousness or awareness monitoring system. System 10 may include a sensor 12 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

An oximeter may include a light sensor that is placed at a site on a patient, typically a fingertip, toe, forehead or earlobe, or in the case of a neonate, across a foot. An oximeter may pass light using a light source through blood-perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as a photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to derive an awareness metric or an amount of a blood constituent (e.g., oxyhemoglobin).

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be a charge-coupled device (CCD) sensor. In another embodiment, the sensor array may be made up of a combination of CMOS and CCD sensors. A CCD sensor may comprise a photoactive region and a transmission region for receiving and transmitting data whereas a CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead. Sensor 12 may also be included in an array of one or more additional types of sensors (e.g., electrodes for sensing electrophysiological signals such as EEG, EMG and/or EOG signals). For example, sensor 12 may be included in a multi-sensor array configured to be located on a patient's head. Additional embodiments are described in detail below.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. Monitor 14 may be configured to calculate physiological parameters based at least in part on data received from any sensor of any type (e.g., an EEG or EMG electrode). For example, monitor 14 may implement a derivation of one or more of a depth of consciousness (DOC) measure (e.g., the BIS index) and an awareness metric, as described herein, to determine information related to a patient's depth of consciousness. In an embodiment, some or all calculations may be performed on sensor 12 itself and the result of the calculations may be passed to monitor 14. Further, monitor 14 may include a display 20 configured to display a patient's physiological parameters or other information about the system. In the embodiment shown, monitor 14 may also include a speaker 22 to provide an audible sound that may be used in various other embodiments, such as sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display information regarding a patient's depth of consciousness, blood oxygen saturation (referred to as an "$SpO_2$" measurement), and/or pulse rate information from monitor 14.

Monitor 14 may be communicatively coupled to multi-parameter patient monitor 26 via a cable 32 or 34 that is coupled to a sensor input port or a digital communications port, respectively, and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

As depicted in FIG. 1, multi-parameter patient monitor 26 may be communicably coupled to electrophysiological sensor 102. This coupling may occur through monitor interface cable 106, which connects to processing module 104, which itself connects to electrophysiological sensor 102 via patient information cable 108. Processing module 104 may perform any of a number of processing operations (e.g., those described below), and may be implemented as described herein with reference to monitor 14. For example, processing module 104 may be a BISx module, which may be configured to identify characteristics of electrophysiological sensor 102 (e.g., sensor arrangement, usage history) and/or to deliver signals (in raw or processed form) from sensor 102 to multi-parameter patient monitor 26. Electrophysiological sensor 102 may include one or more individual electrophysiological sensors (such as electrodes 110, 112 and 114), which may be positioned at one or more body sites on a patient. In an embodiment, multi-parameter patient monitor 26 may display a physiologically-based parameter, such as a BIS index, based at least in part on a signal arising from sensor 102 over an interval of time and at a particular frequency, which may be adjusted by a user (e.g., the last 15 to 30 seconds, and updated every second).

In an embodiment, sensor 102 may be connected directly to multi-parameter patient monitor 26, without the use of processing module 104. In an embodiment, processing module 104 may be included within multi-parameter patient monitor 26. In an embodiment, both sensor 12 and sensor 102 may be communicably coupled to a common processing module (such as processing module 104) which may transmit information based on signals from one or more of the sensors to a monitoring device (such as multi-parameter patient monitor 26). As described above, sensors 12 and 102 may be configured in a unitary sensor body, or may be physically attached to each other. In an embodiment, multi-parameter patient monitor 26 and monitor 14 may be combined into a single monitoring device. It will be noted that any suitable configuration of sensing and monitoring devices adapted to perform the techniques described herein may be used.

Figure 2:
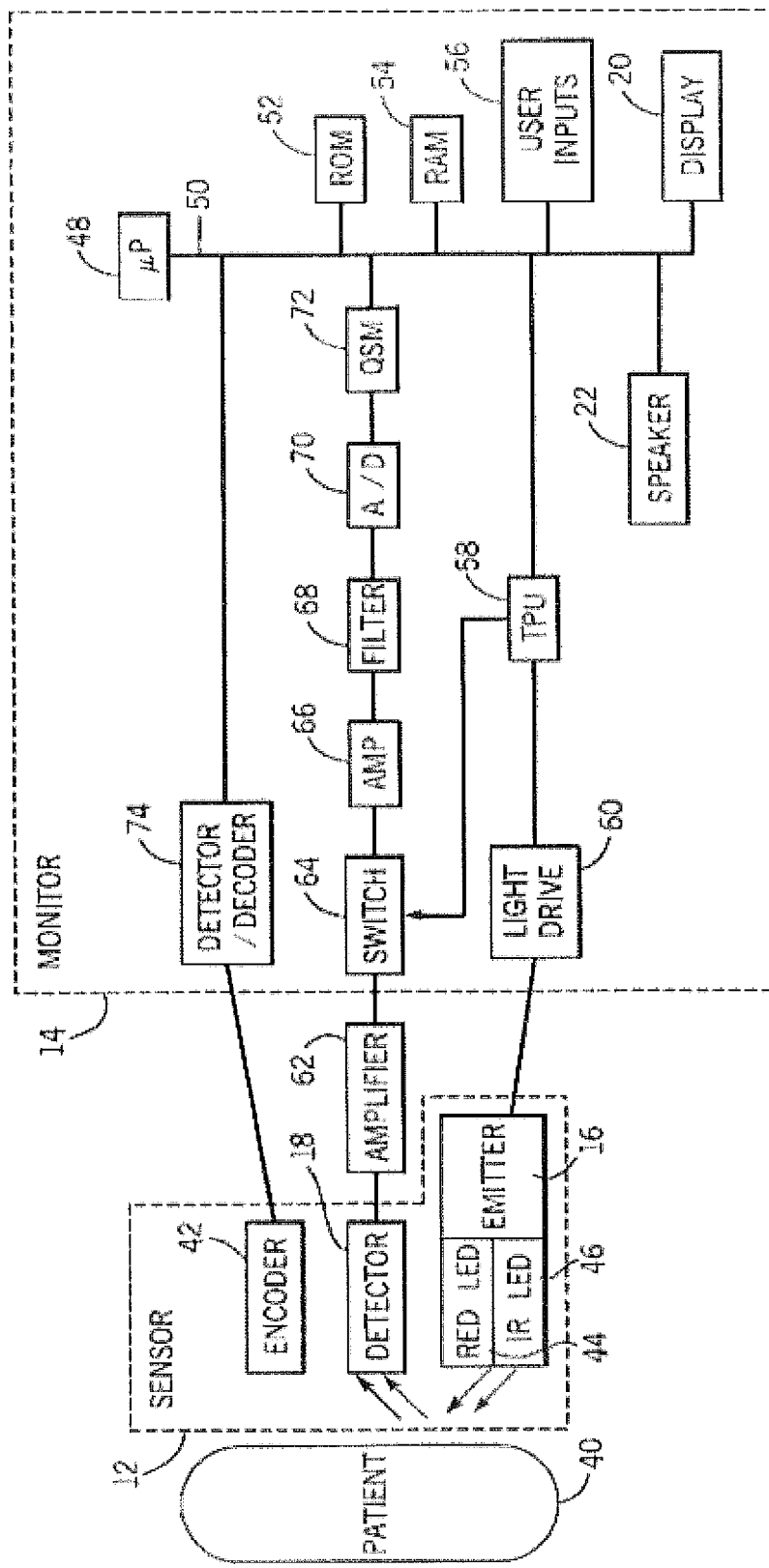
FIG. 2 is a block diagram of a portion of an illustrative patient monitoring system coupled to a patient in accordance with an embodiment.

FIG. 2 is a block diagram of a portion of a patient monitoring system, such as patient monitoring system 10 of FIG. 1, which may be coupled to a patient 40 in accordance with an embodiment. Certain illustrative components of sensor 12 and monitor 14 are illustrated in FIG. 2. It will be noted that although the following discussion of FIG. 2 may refer to components of monitor 14 (FIG. 1) for illustrative purposes, the discussion of these components may also be applied to the components of additional or alternative monitoring devices such as multi-parameter patient monitor 26 (FIG. 1). For example, multi-parameter patient monitor 26 (FIG. 1) may include components analogous to those described with reference to FIG. 2, but configured for use with one or more additional types of sensors, such as electrophysiological sensors.

In an embodiment as depicted in FIG. 2, sensor 12 may include emitter 16, detector 18, and encoder 42. In the embodiment shown, emitter 16 may be configured to emit one or more wavelengths of light (e.g., RED and/or IR) into patient tissue 40. Hence, emitter 16 may include a RED light emitting light source such as RED light emitting diode (LED) 44 and/or an IR light emitting light source such as IR LED 46 for emitting light into patient tissue 40. In one embodiment, the RED wavelength may be between about 600 nm and about 700 nm, and the IR wavelength may be between about 800 nm and about 1000 nm. In other embodiments, emitter 16 may include a light emitting light source of a wavelength other than RED or IR. In embodiments in which a sensor array is used in place of a single sensor, each sensor may be configured to emit a single wavelength. For example, a first sensor may emit only a RED light while a second sensor may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra. Any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths, or any other suitable wavelength. Alternatively, each sensor in the array may be configured to detect an intensity of a single wavelength. In operation, light may enter detector 18 after passing through patient tissue 40. Detector 18 may convert the intensity of the received light into an electrical signal. The light intensity is directly related to the absorbance and/or reflectance of light in tissue 40. For example, in an embodiment in which the emitter and detector are located on opposite sides of a patient's tissue, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption and/or reflection of one or more of the RED and IR (or other suitable) wavelengths in patient tissue 40. In an embodiment, monitor 14 may detect the locations of pulses within the signal received from detector 18. In an embodiment, monitor 14 may calculate one or more awareness metrics based on the signal received from detector 18.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following types of information may be stored for communication to monitor 14: the type of the sensor 12; the wavelength or wavelengths of light emitted by emitter 16; the particular wavelength each sensor in the sensor array is monitoring; a signal threshold for each sensor in the sensor array; the arrangement of sensor 12 and any additional sensors (e.g., electrodes) included in the sensor array; any other suitable information; or any combination thereof.

In an embodiment, signals from detector 18 and encoder 42 may be transmitted to monitor 14. In the embodiment shown, monitor 14 may include general-purpose microprocessor 48 connected to internal bus 50. Microprocessor 48 may be adapted to execute software, which may include an operating system and one or more applications, as part of performing the functions described herein. Also connected to bus 50 may be read-only memory (ROM) 52, random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of system 10. Computer storage media may be located remotely from monitor 14, and arranged to communicate with monitor 14 by a wired or wireless communication protocol.

In the embodiment shown, a time processing unit (TPU) 58 may provide timing control signals to light drive circuitry 60, which may control when emitter 16 is illuminated and multiplexed timing for RED LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as depth of consciousness, awareness, blood pressure, $SpO_2$, and pulse rate, using various algorithms and/or look-up tables based on the value of the received signals and/or data corresponding to the light received by detector 18 (and/or the value of the received signal from any one or more additional sensors in a sensor array, such as an electrophysiological sensor array). In an embodiment, microprocessor 48 may derive one or more awareness metrics based on features of the received signals and/or data. Examples of awareness metrics are discussed below (e.g., with reference to FIG. 5 and FIGS. 6(*a*)-6(*f*)). In an embodiment, microprocessor 48 may derive one or more depth of consciousness (DOC) measures based on one or more received signals. For example, microprocessor 48 may calculate a BIS index using the signal detected by one or more EEG sensors (e.g., arranged in a forehead array).

Signals corresponding to information about patient 40 (e.g., about the intensity of light emanating from a patient's tissue over time) may be transmitted from encoder 42 to decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. Such information may be stored in a suitable memory (e.g., RAM 54) and may allow monitor 14 to determine, for example, patient-specific threshold ranges in which the patient's physiological parameter measurements should fall, and to enable or disable additional physiological parameter algorithms. In an embodiment, display 20 may exhibit a list of values which may generally apply to the patient, such as, for example, age ranges or medication families, which a user may select using user inputs 56.

An optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point at which a sensor is attached. Electromagnetic interference and patient movement may also degrade signals arising from other types of sensors, including motion sensors and electrophysiological sensors (e.g., electrodes).

Noise (e.g., from patient movement) can degrade a physiological signal relied upon by a physician, without the physician's awareness. This is especially true if the monitoring of the patient is remote, the motion is too small to be observed, or the doctor is watching the instrument or other parts of the patient, and not the sensor site. Processing physiological signals may involve operations that reduce the amount of noise present in the signals or otherwise identify noise components in order to prevent them from affecting measurements of physiological parameters derived from the physiological signals.

In an embodiment, one or more of the components of the systems illustrated in FIGS. 1 and 2 may be included in a device used to monitor a depth of consciousness (DOC) of a patient. For example, system 10 may be included in a monitoring system configured to calculate a BIS index value and display one or more depth of consciousness-related parameters (such as an EEG signal) to a care provider. In such an embodiment, components of system 10 may be shared with components of a BIS index monitoring device. For example, display 20 and/or display 28 may be implemented as a display integrated with a BIS index monitoring device. In an embodiment, a BIS index monitoring device may serve as multi-parameter patient monitor 26 of FIG. 1. In an embodiment, one or more components of system 10 (and system 300 of FIG. 3, discussed below) may be implemented as devices configured to communicably couple to a BIS index monitoring device. Such components of system 10 may take the form of an external module that may include sensor 12 and may transmit signals from sensor 12 to a BIS index monitoring device. An external module may also perform one or more signal processing operations on the signal from sensor 12, and may transmit a processed signal to a BIS index monitoring device.

Figure 3:
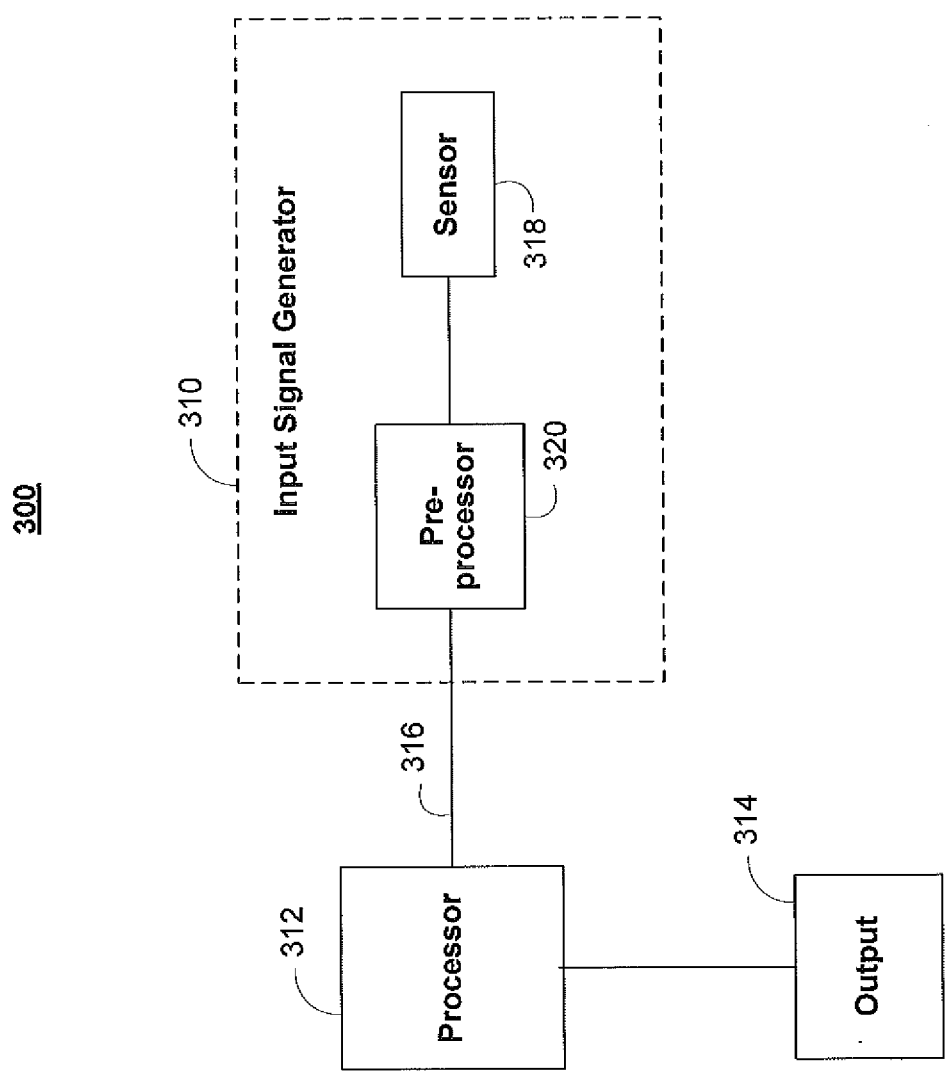
FIG. 3 is a block diagram of an illustrative signal processing system in accordance with an embodiment.

FIG. 3 is an illustrative processing system 300 in accordance with an embodiment. In this embodiment, input signal generator 310 generates input signal 316. As illustrated, input signal generator 310 may include pre-processor 320 (or similar device) coupled to sensor 318, which may provide input signal 316 (e.g., an electrophysiological signal and a PPG signal). In an embodiment, pre-processor 320 may include an oximeter. It will be understood that input signal generator 310 may include any suitable signal source, signal generating data, signal generating equipment, or any combination thereof to produce signal 316. Signal 316 may be any suitable signal or signals, such as, for example, electrocardiogram, electroencephalogram, electrogastrogram, electromyogram, electrooculogram, heart rate signals, accelerometer signals, respiration monitor signals, pathological sounds, ultrasound, any other suitable biosignal, and/or any combination thereof.

In an embodiment, pre-processor 320 may implement a Fast Fourier Transform or Inverse Fast Fourier Transform algorithm to convert the received signal into the frequency domain or time-domain respectively. Pre-processor 320 may include an analog-to-digital converter or digital-to-analog converter for providing a signal to processor 312 in a suitable form. Pre-processor 320 may be, for example, included in processing module 104 as described above with reference to FIG. 1.

In an embodiment, signal 316 may be coupled to processor 312. Processor 312 may be any suitable software, firmware, and/or hardware, and/or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations (e.g., those related to deriving a DOC measure and/or an awareness metric) of the present disclosure, similar to microprocessor 48 (FIG. 2). Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after deriving one or more awareness metrics. Additional filtering operations are discussed below with reference to FIG. 4.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to a DOC measure calculation and/or a awareness metric calculation. In an embodiment, data representing one or more awareness metrics may be stored in RAM or memory internal to processor 312 in any suitable data structure. Memory may be used by processor 312 to store any data related to any of the calculations described herein, and may take the form of any suitable data structure. Processor 312 may be coupled to a calibration device (not shown).

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensors 12 and 102 and monitors 14 and 26, and processor 312 may be implemented as part of monitors 14 and 26. In some embodiments, portions of system 300 may be configured to be portable. For example, all or a part of system 300 may be embedded in a small, compact object carried with or attached to the patient (e.g., a watch, a piece of jewelry, or a cellular telephone). In such embodiments, a wireless transceiver (not shown) may also be included in system 300 to enable wireless communication with other components of system 10. For example, pre-processor 320 may output signal 316 over BLUETOOTH, 802.11, WiFi, WiMax, cable, satellite, Infrared, or any other suitable transmission scheme. In an embodiment, a wireless transmission scheme may be used between any communicating components of system 300. As such, system 10 (FIGS. 1 and 2) may be part of a fully portable and continuous patient monitoring solution.

It will be understood that although each component is drawn separately in FIG. 3, the components may be parts of the same device or may be parts of different devices in various combinations. For example, pre-processor 320 and processor 312 may be implemented by the same circuitry or device. In an embodiment, processor 312 may be implemented by two or more processing devices, which may be communicably coupled. For example, a first processing device may be used to derive a DOC measure based on an electrophysiological measurement, while a second processing device may be used to derive an awareness metric based on another physiological signal, such as a PPG.

In an embodiment, pre-processor 320 may be excluded from system 300 and the physiological signal output by input signal generator 310 may be provided directly to processor 312, which may perform pre-processing operations on the received signal. Pre-processor 320 may output the processed physiological signal to a memory (such as RAM 54 of FIG. 2) for storage, to processor 312, or both.

Processing operations that may be performed on signal 316 are discussed below. It will be understood that such operations may be performed by any suitable component in system 300, such as pre-processor 320 and processor 312. These components may be included in appropriate components of system 10 of FIG. 1 (e.g., monitors 14 and 26). For illustrative purposes only, and not by way of limitation, processing operations may be described as performed by processor 312.

Figure 4:
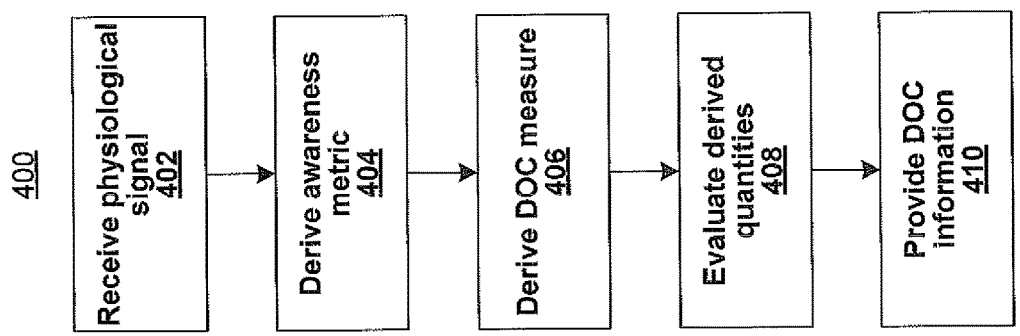
FIG. 4 is a flow chart of illustrative steps performed during depth of consciousness monitoring in accordance with an embodiment.

FIG. 4 depicts a flow chart 400 of illustrative steps involved in depth of consciousness monitoring in accordance with an embodiment. The steps of flow chart 400 may be performed by processor 312, or may be performed by any suitable processing device included in or communicatively coupled to a monitoring device (e.g., monitor 14 (FIGS. 1 and 2) and/or 26 (FIG. 1)). The steps of flow chart 400 may be executed over sliding windows of one or more signals. For example, the steps of flow chart 400 may involve analyzing the previous N samples of a signal, or the signal received over the previous T units of time. The length of a sliding window over which the steps of flow chart 400 may be executed may be fixed or may be dynamic. In an embodiment, the length of a sliding window may be based at least in part on the noise content of a physiological signal. For example, the length of a sliding window may increase with increasing noise. In an embodiment, the length of a sliding window over which the steps of flow chart 400 are executed may be based at least in part on a patient condition. For example, the length of a sliding window may decrease when a patient is undergoing more rapid changes in physiological state, such as regaining consciousness after anesthesia. The length of a sliding window may be different for different received signals, such as an EEG and a PPG signal.

At step 402, a physiological signal may be received. A physiological signal may be one or more electronic signals representative of one or more physiological processes. In an embodiment, a physiological signal may be representative of one or more physiological processes indicative of the depth of consciousness or level of awareness of a patient. A physiological signal may be generated by sensor 12 (FIGS. 1 and 2) and/or sensor 102 (FIG. 1), which may be implemented, for example, as any of the sensor arrangements described herein. A physiological signal may be signal 316 (FIG. 3), which may be generated by pre-processor 320 (FIG. 3) coupled between processor 312 (FIG. 3) and sensor 318 (FIG. 3). A physiological signal may include multiple signals, for example, in the form of a multi-dimensional vector signal, signals over multiple signal lines, or a frequency- or time-multiplexed signal. Additionally, a physiological signal received at step 402 may be generated internally to processor 312 (FIG. 3). For example, the received signal may be based at least in part on past values of a physiological signal, which may be retrieved by processor 312 (FIG. 3) from a memory such as a buffer memory or RAM 54 (FIG. 2).

In an embodiment, a signal received at step 402 may include a PPG signal which may be obtained from sensor 12 (FIGS. 1 and 2) which may be coupled to a patient. In an embodiment, a signal received at step 402 may include an electrophysiological signal, which may be obtained from electrophysiological sensor 102 (FIG. 1) coupled to a patient. In an embodiment, the signal received at step 402 may include both a PPG signal (e.g., from a forehead oximeter) and one or more electrophysiological signals (e.g., from a forehead electrode array). In an embodiment, the signal may be received at step 402 in real time. In an embodiment, the signal may have been stored in ROM 52 (FIG. 2), RAM 52 (FIG. 2), and/or QSM 72 (FIG. 2) in the past and may be accessed by a microprocessor such as microprocessor 48 (FIG. 2) within monitor 14 (FIGS. 1 and 2) to be processed. One or more physiological signals may be received at step 402 (e.g., as part of input signal 316 (FIG. 3)) and may include one or more of a Red PPG signal and an IR PPG signal.

In an embodiment, a signal received at step 402 may be filtered using any suitable filtering technique. For example, a signal obtained from sensor 12 (FIGS. 1 and 3) may be filtered by low pass filter 68 (FIG. 2) prior to undergoing additional processing at microprocessor 48 (FIG. 2) within patient monitoring system 10 (FIGS. 1 and 2). Low pass filter 68 (FIG. 2) may selectively remove frequencies that may later be ignored by a transformation or other processing step, which may advantageously reduce computation time and memory requirements. In an embodiment, a signal received at step 402 may be high-pass, comb or band-pass filtered. A high-pass filter may be, for example, a derivative filter. In an embodiment, a signal received at step 402 may be filtered to remove a DC component. In an embodiment, the cutoff frequencies of a filter may be chosen based on the frequency response of the hardware platform underlying system 10 (FIGS. 1 and 2). In an embodiment, a signal received at step 402 may be normalized by dividing the signal by a DC component.

In an embodiment, a signal received at step 402 may be transformed. A transformation may occur in conjunction with the receiving at step 402, or after the signal is received at step 402. In an embodiment, processor 312 (FIG. 3) may transform the signal into any suitable domain, for example, a Fourier, wavelet, spectral, scale, time, time-spectral, time-scale domain, or any transform space. This transformation may be performed by any suitable processing device, such as processor 312 (FIG. 3) and/or microprocessor 48 (FIG. 2), either of which may be a general-purpose computing device or a specialized processor. The transformation may also be performed by a separate, dedicated device. Processor 312 (FIG. 3) may further transform the original and/or transformed signals into any suitable domain. In an embodiment, a transformation may be based at least in part on a continuous wavelet transformation. In an embodiment, a transformation may include performing a continuous wavelet transform for one or more physiological signals received at step 402, which may include one or more electrophysiological signals, an IR PPG signal, a Red PPG signal, or any combination of signals.

In an embodiment, pre- or post-processing techniques may be applied to a signal received at step 402. These techniques may include any one or more of the following: compressing; multiplexing; modulating; up-sampling; down-sampling; smoothing; taking a median or other statistic of the received signal; taking one or more derivatives of the received signal (e.g., with respect to time, space and/or scale); removing erroneous points or regions of the received signal; or any combination thereof. In an embodiment, a normalization step may be performed which divides the magnitude of the received signal by a value. This value may be based on at least one of the maximum of the received signal, the minimum of the received signal and the mean of the received signal.

Different operations, which may include transformation, processing and/or filtering techniques, may be applied to any one or more of the components of a multi-component signal received at step 402. For example, different operations may be applied to one or more electrophysiological signals, a Red PPG signal and an IR PPG signal. An operation may be applied to a portion or portions of a received signal. An operation may be broken into one or more stages performed by one or more devices within signal processing system 300 (FIG. 3) (which may itself be a part of patient monitoring system 10 (FIGS. 1 and 2)). For example, a filtering technique may be applied by input signal generator 310 (FIG. 3) prior to passing the resulting signal 316 (FIG. 3) to processor 312 (FIG. 3), where it may undergo a transformation. Embodiments of the steps of flow chart 400 include any of the operations described herein performed in any suitable order.

Any number of computational and/or optimization techniques may be performed in conjunction with the techniques described herein. For example, any known information regarding the physiological status of the patient may be stored in memory (e.g., ROM 52 or RAM 54 of FIG. 2). Such known information may be keyed to the characteristics of the patient, which may be input via user inputs 56 (FIG. 2) and used by monitor 14 (FIGS. 1 and 2) to, for example, query a lookup table and retrieve the appropriate information. Additionally, any of the techniques described herein may be optimized for a particular hardware implementation, which may involve implementing any one or more of a pipelining protocol, a distributed algorithm, a memory management algorithm, or any suitable optimization technique.

Once a physiological signal is received at step 402, an awareness metric may be derived at step 404 based at least in part on the physiological signal. An awareness metric may be any quantification of a feature or features in the physiological signal or a transformation of the physiological signal that indicates the level of awareness (or depth of consciousness) of a patient. In an embodiment, an awareness metric may be derived from one or more PPG signals included in the physiological signal received at step 402. An awareness metric may be derived by any suitable processor, such as microprocessor 48 (FIG. 2), or may be extracted by special-purpose analog hardware. In an embodiment, an awareness metric may be calculated over a portion of the physiological signal within a time window. Generally, "time window" may be used to refer to either an interval of time, a number of pulses or periods of a periodic signal, or a combination of the two. In an embodiment, an awareness metric may be calculated over a single pulse or multiple pulses within a PPG signal, representing one or more cardiac pulses. The time window over which an awareness metric may be derived may include past values of a physiological signal. In an embodiment, an awareness metric is first calculated from the physiological signal over each of a first time window and a second time window, then the values of the awareness metric over each window are combined (e.g., by taking a difference, an absolute difference, an average, or a ratio).

Figure 5:
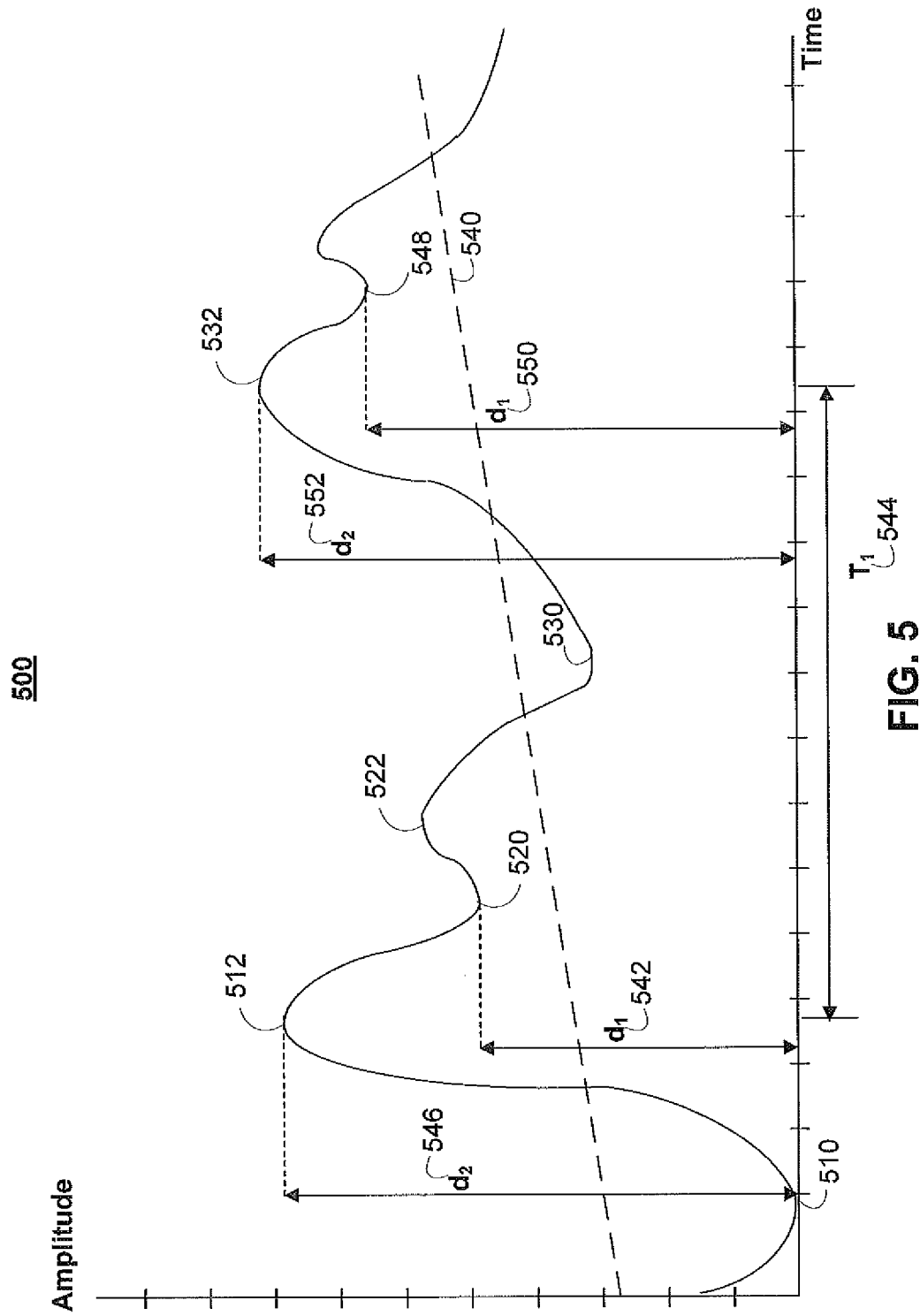
FIG. 5 depicts features of an illustrative physiological signal in accordance with an embodiment.
Figure 6A:
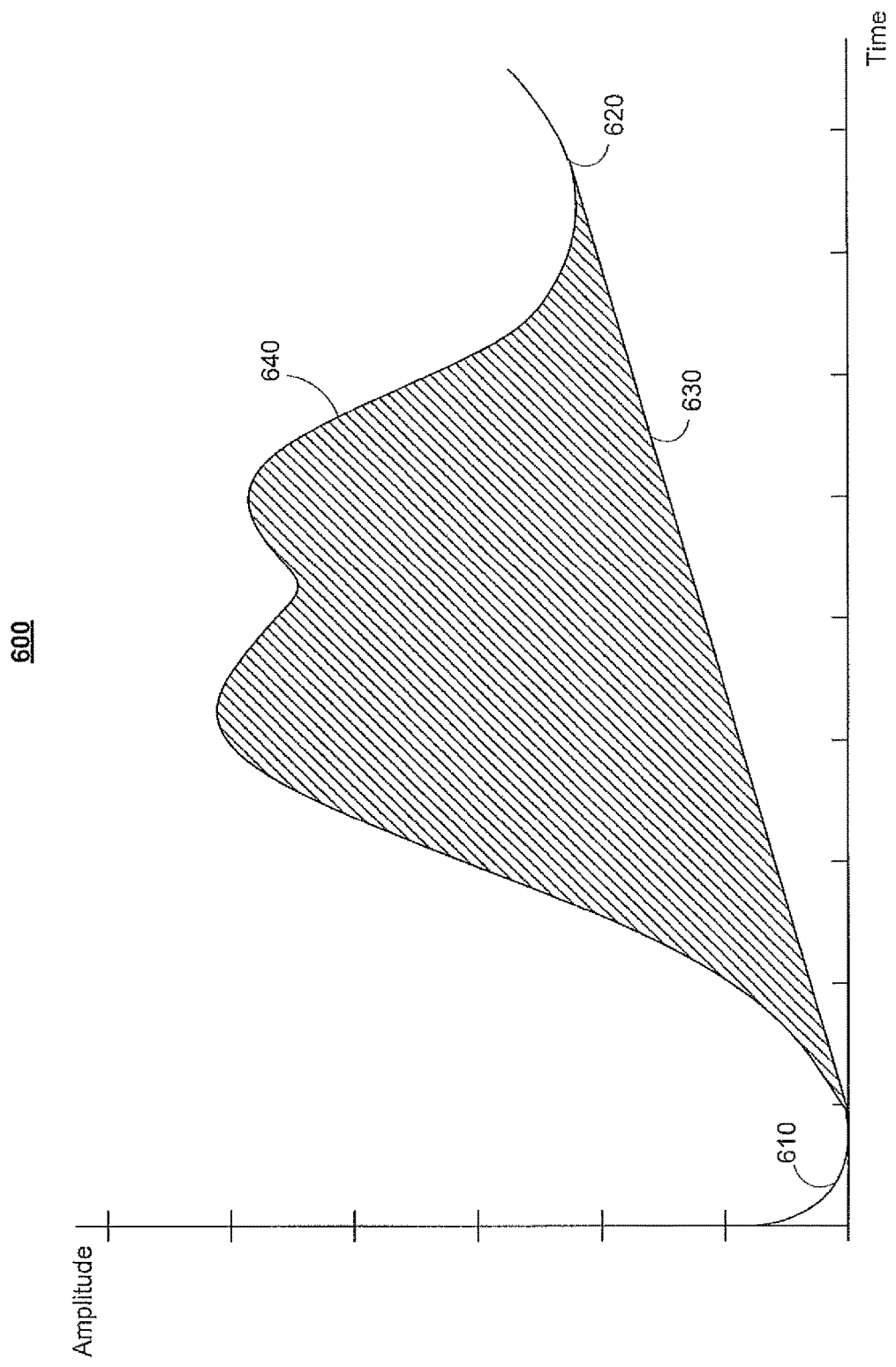
FIGS. 6(*a*)-6(*f*) depict illustrative areas that may be used in the derivation of an awareness metric in accordance with an embodiment.
Figure 6B:
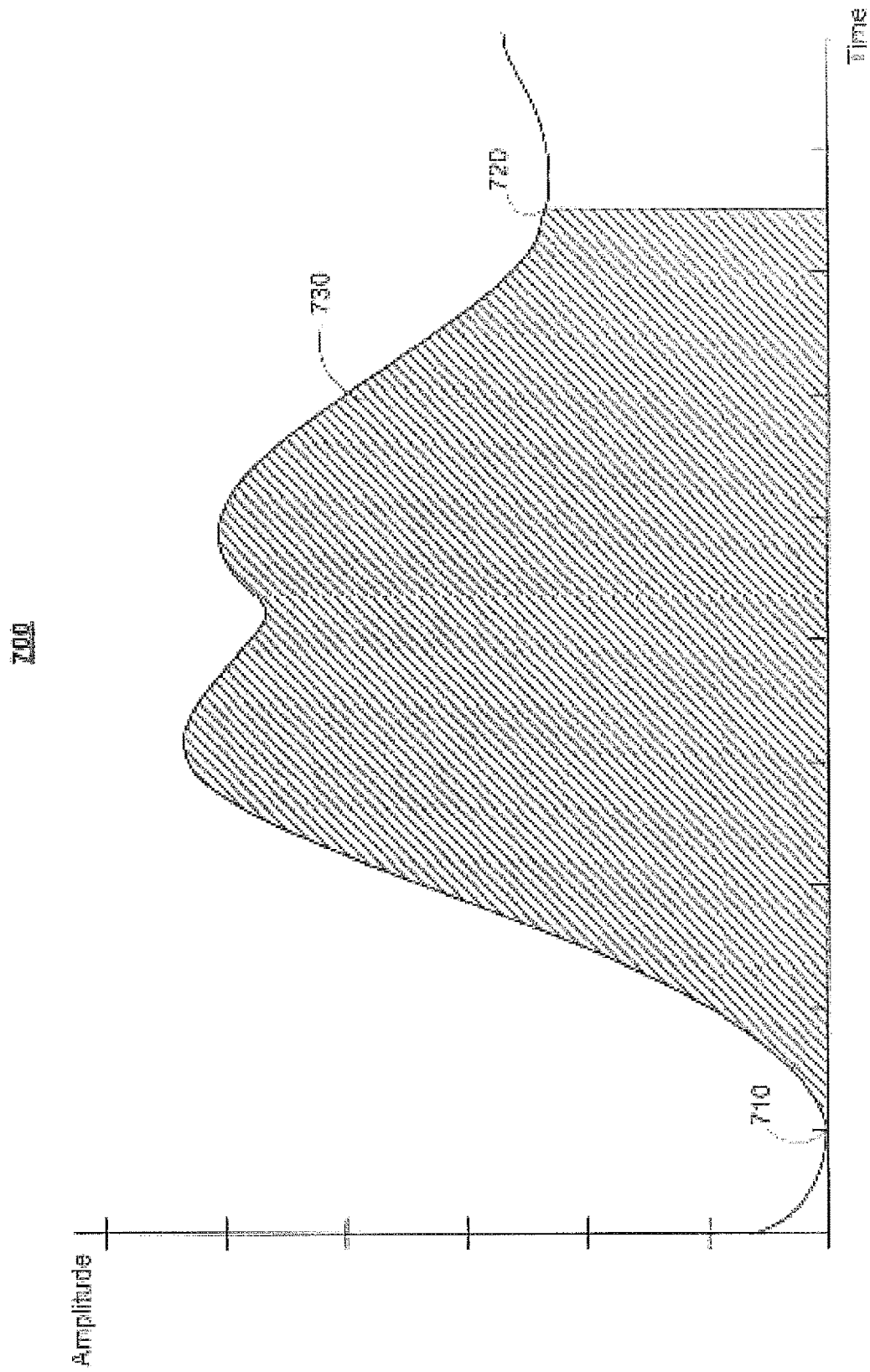
Figure 6C:
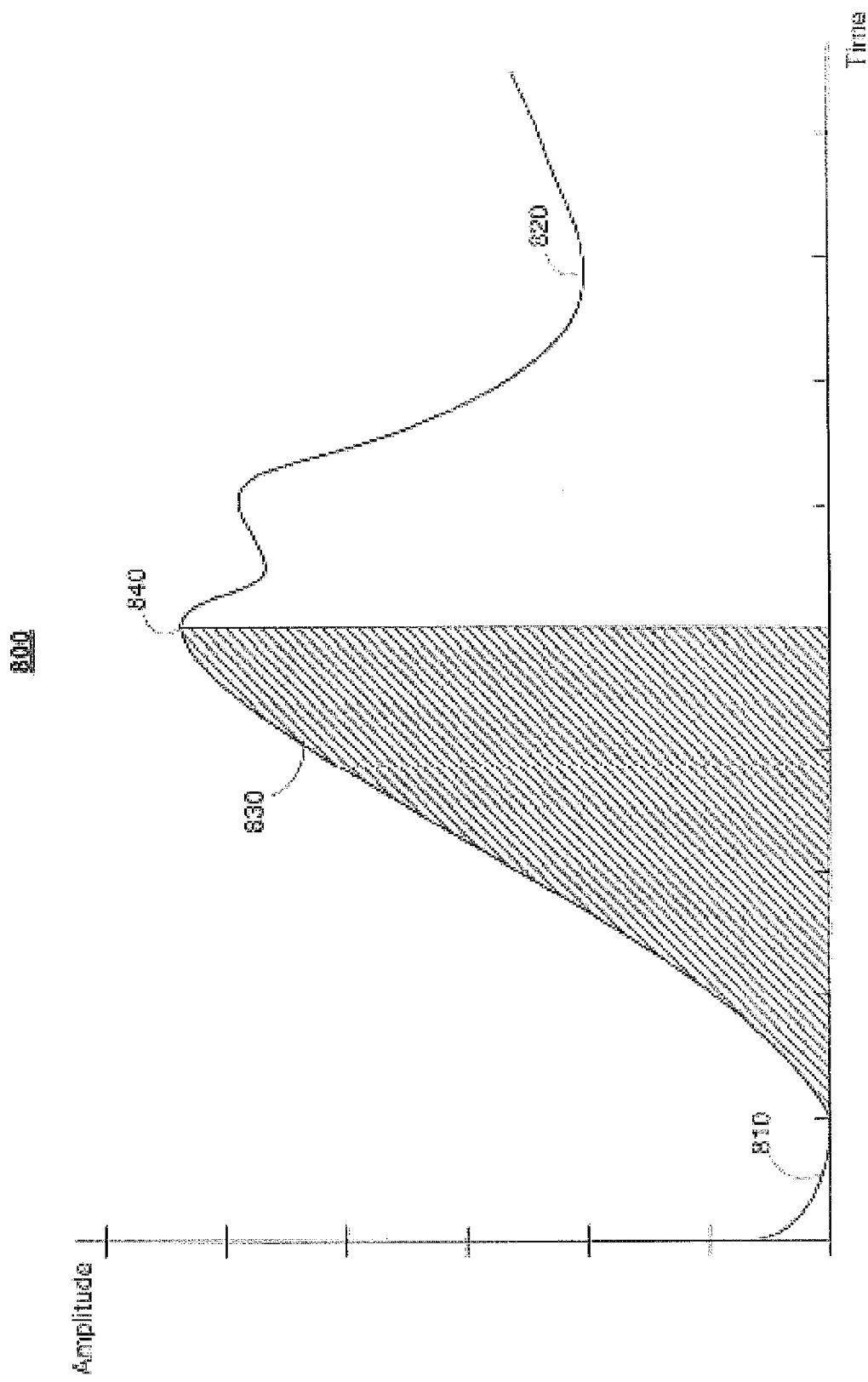
Figure 6D:
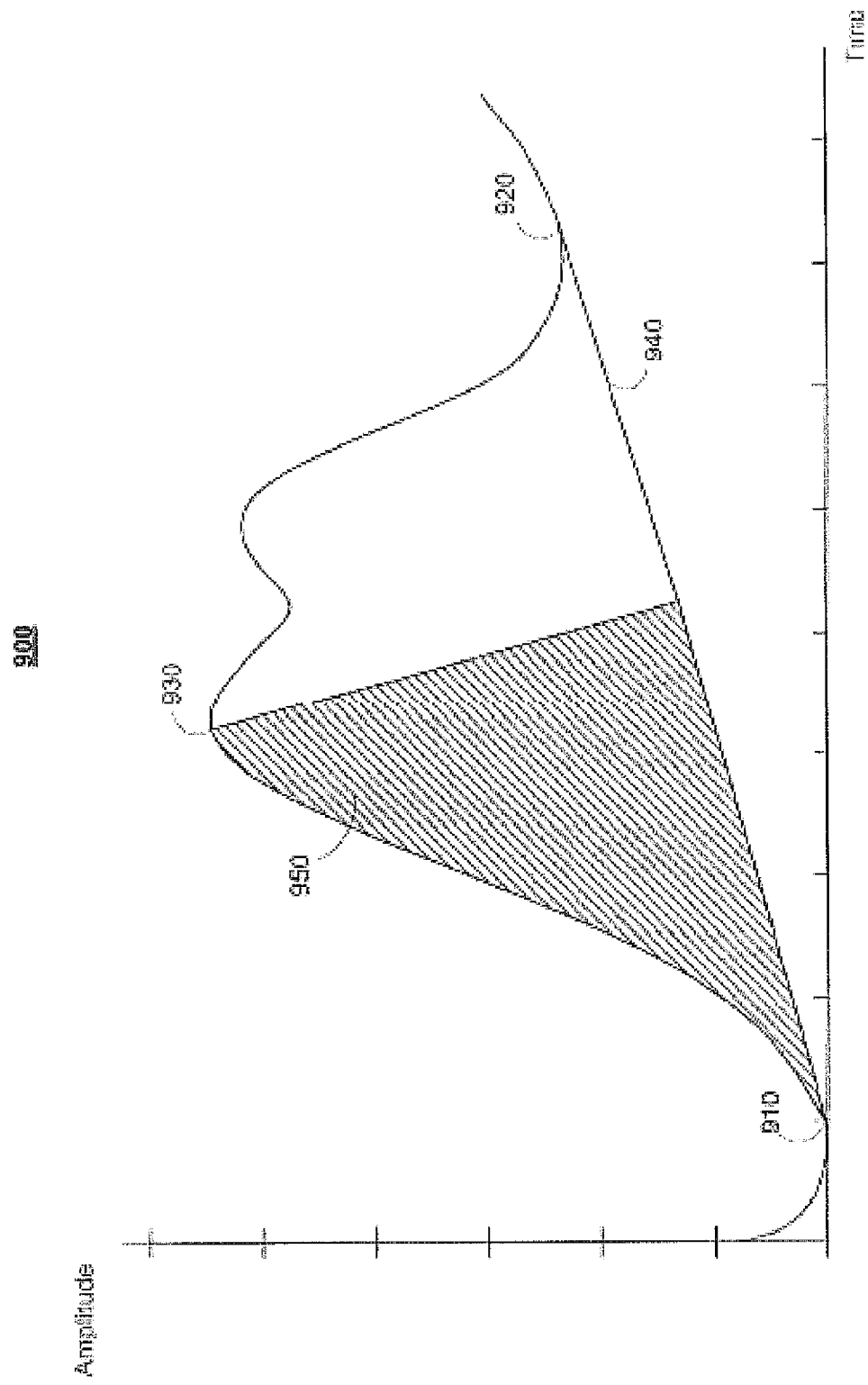
Figure 6E:
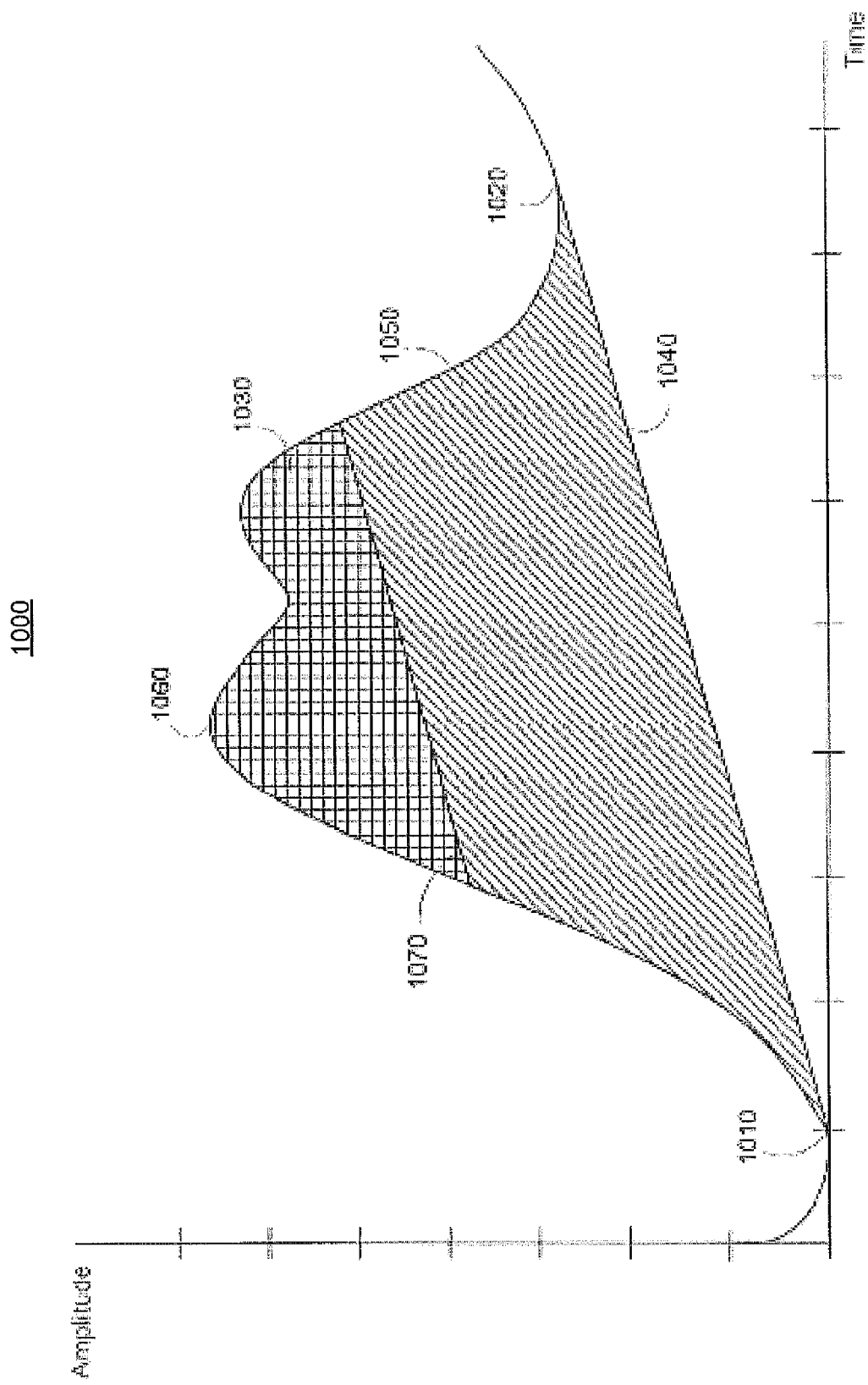

An awareness metric derived at step 404 may depend at least in part on one or more features of the physiological signal received at step 402. FIG. 5 and FIGS. 6(*a*)-6(*f*) illustrate features of a physiological signal that may be used in the derivation of an awareness metric at step 404 in accordance with the present disclosure. It will be understood that these features are only examples, and that any suitable feature or features of a physiological signal that contain information about a patient's level of awareness (or depth of consciousness) may be used with the techniques described herein.

Local minima and local maxima points may be identified as features in a physiological signal. For example, microprocessor 48 (FIG. 2) may compute the first or second derivative of the physiological signal (or a portion thereof) to identify turning points in the physiological signal. In one suitable approach, local minimum and local maximum points may be defined as turning points (i.e., points in the physiological signal where the slope changes from positive to negative or negative to positive). For example, as shown in illustrative signal 500 of FIG. 5, points 510, 520 and 530 may be identified as local minima points while points 512, 522 and 532 may be identified as local maxima points. Local or global extrema may indicate a change in a physiological parameter associated with a change in awareness, such as blood pressure, vasotone, compliance, heart rate, and/or cardiac output.

Pulses may be identified as features in a physiological signal. A pulse may include at least one upstroke segment and at least one adjacent downstroke segment (which may be identified, for example, by local minima and maxima points or any other suitable technique). Within a pulse, there may be further combinations of smaller upstroke and downstroke segments which may indicate dichrotic, shoulder and/or ankle notches of a PPG signal (depending on the locations of the segments). For example, point 520 may represent a dichrotic notch in a PPG signal. A ratio of a duration of the downstroke and a duration of the upstroke from one or more pulses may be identified as a feature in a physiological signal. Features indicative of the changing morphology of the pulses may indicate a change in a physiological parameter associated with a change in awareness, such as blood pressure, vasotone, compliance, heart rate, and/or cardiac output. Techniques for identifying pulses in physiological signals are described in Watson, U.S. application Ser. No. 12/242,908, filed Sep. 30, 2008, entitled "SYSTEMS AND METHODS FOR DETECTING PULSES," which is incorporated by reference herein in its entirety.

Characteristic amplitudes may be identified as features in a physiological signal. A characteristic amplitude may include a peak amplitude, a minimum amplitude, or a mean amplitude. Amplitude, or changes in amplitude, may indicate a change in a physiological parameter associated with a change in awareness, such as blood pressure, vasotone, compliance, heart rate, and/or cardiac output. A baseline value may be identified, which may be defined as the mean minimum amplitude over a time window or a mean amplitude over a time window (or running mean, as illustrated by dashed line 540). A baseline of a pulse may also be defined by a line extending from a starting point of the pulse to an ending point of the pulse, as discussed below.

The period of a pulse and/or the frequency of pulses may be identified as features in a physiological signal. For example, the period of the pulse identified between local maxima 512 and 532 is indicated by $T_1$ 544. The path length of a pulse, defined as the sum of the absolute values of the differences between subsequent samples taken over the duration of the pulse, may be identified as a feature in a physiological signal. Period or frequency of pulses may be used to determine heart rate, which may itself be a feature in a physiological signal. It is known, for example, that patient arousals during sleep may cause an associated increase in heart rate.

An augmentation index may be identified as a feature in a physiological signal. An augmentation index may be calculated as the ratio of the height at a dichrotic notch in a PPG signal to the cardiac pulse height. For example, if signal 500 represents a PPG signal, an augmentation index at the dichrotic notch represented by point 520 may be calculated as the ratio of $d_1$ 542 to $d_2$ 546. In another example, an augmentation index at the dichrotic notch represented by point 548 may be calculated as the ratio of $d_1$ 550 to $d_2$ 552. An augmentation index calculated from a PPG signal may be indicative of the compliance of a patient's circulatory system.

FIGS. 6(*a*)-6(*f*) depict illustrative physiological signal pulses 600-1100 whose areas may be computed (e.g., by processor 312 of FIG. 3) as features in a physiological signal. In particular, each pulse 600-1100 shows a different area that may be measured and used as a feature when deriving an awareness metric. Although only one pulse is shown and described below in the context of the disclosure, it should be understood that the areas of multiple pulses may be measured and used in an awareness metric, for example, by using the median, maximum, minimum, average, or any other suitable function of multiple pulse area measurements. Different areas, comparisons between different areas, or changes in area may indicate a change in a physiological parameter associated with a change in awareness, such as blood pressure, vasotone, compliance, heart rate, and/or cardiac output.

In some embodiments, the area of a pulse may be measured relative to a baseline of the pulse. Pulse 600 of FIG. 6(*a*) is illustrative of an embodiment. Pulse 600 includes a starting point 610, an ending point 620 and a baseline 630 which is represented by a line segment connecting the starting and ending points of the pulse. Area 640 may be the area of the entire pulse (between points 610 and 620) relative to baseline 630. A similar area of one or more subsequent pulses may also be measured relative to baseline 630 or relative to their respective baselines. The mean, max, min, average or some other suitable value may be computed between the one or more areas (i.e., the area of the first pulse and the areas of one or more subsequent pulses). Processor 312 (FIG. 3) may use the mean, max, min, average or other suitable value in an awareness metric derivation.

In some embodiments, the area of a signal pulse may be measured relative to a time-domain axis. Pulse 700 of FIG. 6(*b*) is illustrative of an embodiment. Pulse 700 includes a starting point 710 and an ending point 720. Area 730 is the area of the entire pulse 700 (between points 710 and 720) relative to a constant-valued baseline defined by a minimum value of the pulse, or alternatively, the time-domain axis. A similar area of one or more subsequent pulses may be measured relative to a similar, subsequently-derived constant-valued baseline. The mean, max, min, average or some other suitable value may be computed between the multiple areas (i.e., the area of the first pulse and the areas of one or more subsequent pulses) by processor 312 (FIG. 3). Processor 312 (FIG. 3) may use the mean, max, min, average or other suitable value in an awareness metric derivation.

In some embodiments, the area of an upstroke or downstroke of a physiological signal pulse may be measured relative to a constant-valued baseline or time-domain axis of the pulse. Pulse 800 of FIG. 6(*c*) is illustrative of an embodiment. Pulse 800 includes a starting point 810, ending point 820 and maximum point 840. Area 830 of the pulse represents the area of the pulse corresponding to the upstroke of the pulse (e.g., the area between the starting point 810 of the pulse and the maximum point 840 of pulse 800 relative to a constant-valued baseline with an amplitude value having the same value as point 810). Similarly, an area of the pulse corresponding to the downstroke of the pulse may be measured (e.g., the area between the maximum point 840 and the ending point 820 of pulse 800 relative to the constant-valued baseline with an amplitude value having the same value as point 820). The area of one or more subsequent upstrokes or downstrokes of one or more pulses may also be measured relative to the similarly derived constant-valued baseline. The mean, max, average or some other suitable value may be computed between the multiple areas (i.e., the area of the upstroke or downstroke of the first pulse and the areas of the upstrokes or downstrokes of one or more subsequent pulses) by processor 312 (FIG. 3). Processor 312 (FIG. 3) may use the mean, max, min, average or other suitable value in an awareness metric derivation.

In some embodiments, the area of an upstroke or downstroke of the pulse may be measured relative to a baseline of the pulse. Pulse 900 of FIG. 6(*d*) is illustrative of an embodiment. Area 950 may be measured from the portion under pulse 900 between baseline 940, maximum point 930 and starting point 910. Area 950 may represent the area of the pulse corresponding to the upstroke of the pulse relative to the baseline. Similarly, an area of the pulse corresponding to the downstroke of the pulse may be measured for an area covered between the line extending from maximum point 930 and ending point 920. The area of one or more subsequent upstrokes or downstrokes of one or more pulses may also be measured relative to baseline 940 or their respective baselines. The mean, max, min, average or some other suitable value may be computed between the multiple areas (i.e., the area of the upstroke or downstroke of the first pulse and the areas of the upstrokes or downstrokes of one or more subsequent pulses) by processor 312 (FIG. 3). Processor 312 (FIG. 3) may use the mean, max, min, average or other suitable value in an awareness metric derivation.

In some embodiments, a PPG signal pulse may be split into different sections and the area of each section may be used in an awareness metric derivation. For example, pulse 1000 of FIG. 6(*e*) is depicted as split into two sections. The pulse may be split along segment 1070 which may extend from an approximate midpoint of the upstroke of the pulse (a point between the starting point 1010 and maximum point 1060) to an approximate midpoint of the downstroke of the pulse (a point between maximum point 1060 and end point 1020).

Although segment 1070 extending from the midpoint is drawn parallel to baseline 1040, it should be understood that segment 1070 may be drawn at any angle relative to baseline 1040 without departing from the scope of this disclosure. It should also be understood that although segment 1070 is shown and described as extending from the midpoint of the upstroke of the pulse, segment 1030 (or segment 1050) may extend from any point along the upstroke of the pulse to any point along the downstroke of the pulse to split the pulse into two sections. For example, the pulse may be split with a segment drawn from the starting point of a dichrotic or some other notch in the pulse parallel to the baseline or with some other suitable slope. It should also be understood that the areas of each section of the split pulse may be measured relative to the time-domain axis as discussed above.

In some embodiments, the pulse may be split into three sections and the areas of two of the three sections may be measured and used in an awareness metric derivation. For example, two segments may be drawn, one extending from slightly above the midpoint and one extending from slightly below the midpoint forming an upper section and a lower section separated by a middle section. The areas of the upper section and lower sections may be used in an awareness metric while the middle section may be ignored. Alternatively, any combination of two of the three sections may be measured and used in an awareness metric derivation.

The areas of multiple pulses and their respective sections may be similarly measured and a mean, median, average, maximum, or some other suitable value may be computed between the multiple respective areas. Processor 312 (FIG. 3) may use the mean, max, min, average or other suitable value in an awareness metric derivation.

In some embodiments, pulse 1000 may be filtered such that the pulse is aligned along the time-domain axis as shown in FIG. 6(*f*) as pulse 1100. In particular, a filter or some other suitable technique may be applied to pulse 1000 to cause the portion of the pulse that is above the segment 1080 (corresponding to segment 1070 of FIG. 6(e)) extending from the midpoint of the pulse to be positioned above the time-domain axis (such that it corresponds to positive amplitudes) and the section below the midpoint to be positioned below the time-domain axis (such that it corresponds to negative amplitudes). This may simplify measuring areas of multiple pulses because all of the positive areas of the multiple pulses may correspond to the upper pulse sections and all of the negative areas of the multiple pulses may correspond to the lower pulse sections. A mean, max, median, min, or some other suitable value may more easily be computed from the multiple area measurements. Processor 312 (FIG. 3) may use the mean, max, min, average or other suitable value in an awareness metric derivation. Techniques for calculating areas of physiological signals are described in Sethi, U.S. application Ser. No. 12/242,867, filed Sep. 30, 2008, entitled "SYSTEMS AND METHODS FOR NON-INVASIVE CONTINUOUS BLOOD PRESSURE DETERMINATION," which is incorporated by reference herein in its entirety.

The skewness of a physiological signal may be identified as a feature in a physiological signal. Skewness generally refers to the asymmetry of a signal around its mean or average value, and may capture, for example, the initial highly negative portion and subsequent smaller positive portion of a pulse of a PPG time derivative signal. Other skewness measures that capture this feature may include the ratio of the positive area or peak of a PPG time derivative signal to the negative area or peak of a PPG time derivative signal, or the ratio of the duration of the upstroke to the duration of the downstroke of a PPG signal. Examples of skewness calculations that may be used in accordance with the techniques provided herein are described in Watson et al., U.S. patent application Ser. No. 12/494,971, filed Jun. 30, 2009, entitled "SYSTEMS AND METHODS FOR ASSESSING MEASUREMENTS IN PHYSIOLOGICAL MONITORING DEVICES," which is incorporated by reference herein in its entirety. A long-term change in skewness may indicate a change in signal morphology, which in turn may indicate a change in, for example, blood vessel compliance.

As described above, an awareness metric may quantify any one or more features of a physiological signal indicative of a patient's level of awareness. As such, an awareness metric may be based on one or more features which indirectly or directly convey information about patient awareness. For example, a pulse rate may be obtained from a PPG signal and used to determine whether a patient is in a low awareness state (e.g., when the pulse rate is below a nominal, waking value). An awareness metric may also quantify a change in one or more features of a physiological signal over time, which may also convey information about patient awareness.

In an embodiment, a pulse transit time (PTT) waveform may be used to indicate a patient's level of awareness. A PTT waveform may represent a time difference between a first pulse event and second pulse event. For example, pulse transit time or any other suitable time difference may be computed as the time difference between a first identified characteristic point from a filtered PPG signal derived from a PPG signal generated by a first sensor and a second identified characteristic point from a filtered PPG signal derived from a PPG signal generated by a second sensor. A PTT waveform may exhibit features indicative of microarousal activity (i.e., a brief period of awakening, sometimes clinically characterized by EEG activity), and thus awareness. Examples of PTT calculations that may be used in accordance with the techniques provided herein are described in Watson et al., U.S. patent application Ser. No. 12/568,946, filed Sep. 29, 2009, entitled "SYSTEMS AND METHODS FOR HIGH-PASS FILTERING A PHOTOPLETHYSMOGRAPH SIGNAL," which is incorporated by reference herein in its entirety.

In an embodiment, a pulse effort signal may be used to indicate a patient's level of awareness (e.g., as a proxy for a PTT waveform). An effort signal may relate to a measure of strength of at least one repetitive feature in a signal, such as pulses or respiration features in a PPG signal. In another embodiment, effort may relate to physical effort of a process that may affect the signal (e.g., effort may relate to work of a process). An effort may be based on a scalogram derived from a continuous wavelet transform of a signal such as a PPG signal. Examples of effort signal derivations that may be used in accordance with the techniques provided herein are described in Addison et al., U.S. application Ser. No. 12/245,366, filed Oct. 3, 2008, entitled "SYSTEMS AND METHODS FOR DETERMINING EFFORT," which is incorporated by reference herein in its entirety. Monitoring respiratory effort may be particularly useful when a patient is becoming aware and beginning to breathe by himself or herself.

In an embodiment, vasoconstriction, which may be caused by an arousal from sleep or an unconscious state and thus correspond to an increase in awareness, may manifest itself in a PPG waveform as a change in pulse morphology. For example, vasoconstriction may be indicated by a reduced cardiac pulse amplitude, or a change in augmentation index. In an embodiment, a change in cardiac output (e.g., an increase) may also be used as an indication of arousal or increased awareness. A change in cardiac output may be manifest in PPG signal features as an increased pulse rate and/or a decreased pulse amplitude. Further, increased venous return, which may be linked to cardiac output, may also manifest itself as one or more features in a physiological signal. For example, increased venous return may contribute to or alter a baseline value of a PPG signal. One mechanism for this relationship may be that increased venous return implies less venous pooling, which in turn may lead to more light transmitted through a patient's tissue (e.g., a finger) during an oximetry reading and thus a change in a PPG baseline.

Accordingly, in an embodiment, an awareness metric may detect one or more features of a physiological signal related to a change in vasotone. Such a metric may, for example, quantify a change in a baseline value of a PPG signal, a change in heart rate (e.g., as determined from a PPG signal, a blood pressure signal, or any other physiological signal capable of communicating heart rate information), a change in or value of an augmentation index of a PPG signal, a change in an area of a pulse of a physiological signal, a change in a pulse amplitude, a change in a notch position, any other suitable feature or change in features, or any combination of the above.

Awareness metrics may also include normalized and generalized versions of metrics described herein, and may be applied to one or more pulses or time windows and combined via any suitable transformation. For example, an awareness metric may be based at least in part on a change of shape between two instances or windows of a physiological signal received at step 402 of FIG. 4. An awareness metric may be based on a linear or non-linear combination or comparison of two or more components of a physiological signal received at step 402 (e.g., an electrophysiological signal and a PPG signal).

Figure 7:
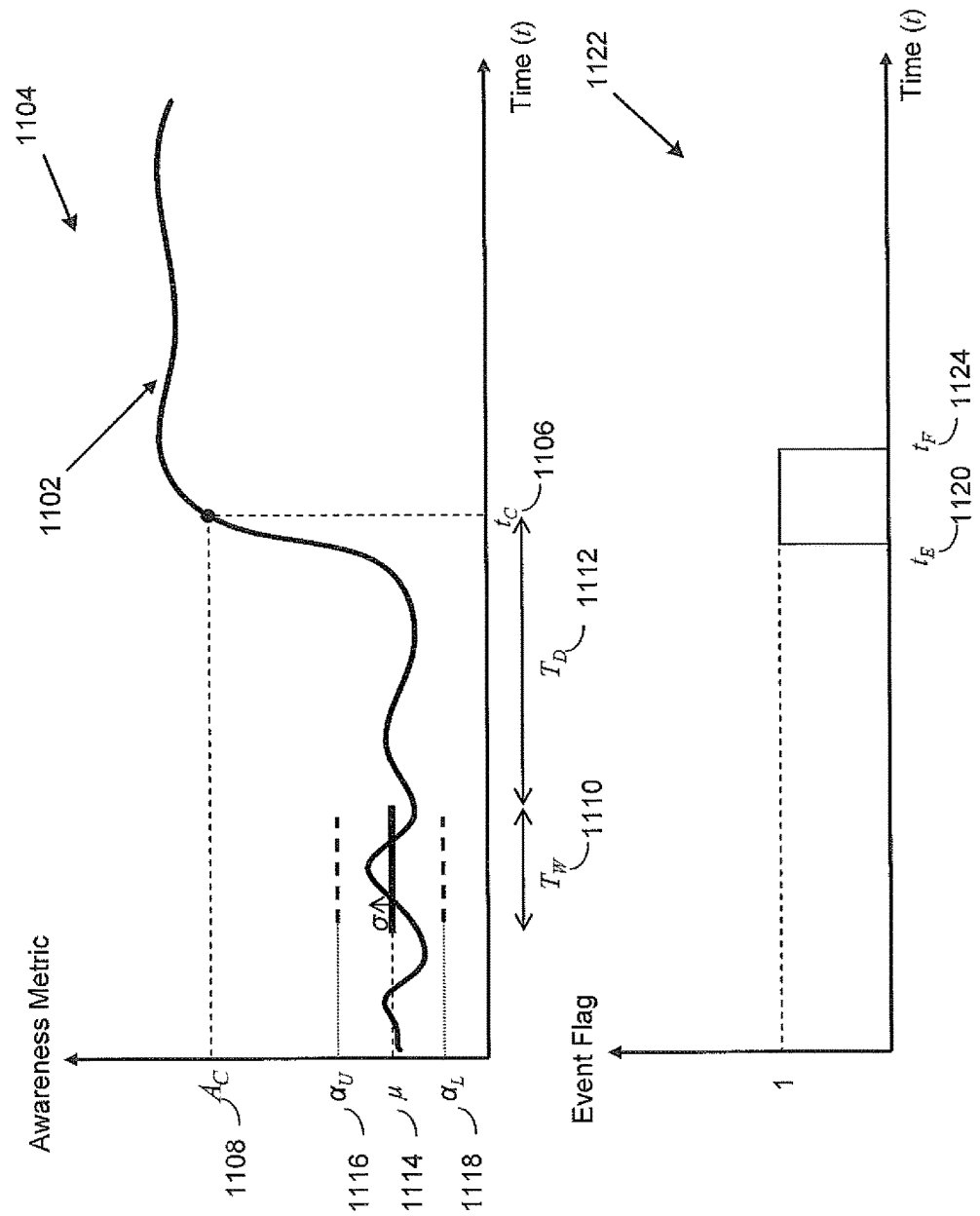
FIG. 7 depicts an illustrative awareness metric waveform and an illustrative awareness event flag in accordance with an embodiment.

In an embodiment, an awareness metric may be derived over time (continuously or at discrete time instances). A time sequence of such values may be combined to form a time-dependent awareness metric waveform. FIG. 7 depicts illustrative awareness metric waveform 1102. The particular shape of awareness metric waveform 1102 depicted in plot 1104 is simply illustrative; an awareness metric waveform may be calculated in accordance with any of the techniques described herein, and may have any resulting shape. As discussed below, in an embodiment, an awareness metric waveform may be used at step 408 (FIG. 4) to evaluate derived quantities.

At step 406 of FIG. 4, one or more DOC measures may be derived. A DOC measure is any measure or index of a patient's depth of consciousness. For example, a DOC measure may be a BIS index, as discussed previously. In an embodiment, the physiological signal received at step 402 may include an electrophysiological signal (e.g., from a forehead sensor) and a DOC measure may be based on the electrophysiological signal, which may include one or more of an EEG signal, an EMG signal and an EOG signal. In an embodiment, a DOC measure may be based on a respiratory signal, such as a signal representing the rise and fall of a patient's chest during respiration as measured by a transducer attached to a chest or abdominal strap; temperature changes in a patient's nasal or oral cavities as measured by a thermocouple; or pressure/airflow changes measured by, for example, one or more transducers in the respiratory tract. In an embodiment, a DOC measure derived at step 406 may be based on a physiological signal received at step 402, and may differently quantify features of the signal than the awareness metric derived at step 404. As described above, a BIS index may be derived utilizing a composite of measures from EEG and physiological signal processing techniques including bispectral analysis, power spectral analysis, and time domain analysis. In another example, a derived awareness metric may be based on a time-domain analysis of the received signal, while a DOC measure may be based on a spectral domain analysis. In another example, a derived awareness metric may use a first feature of a received signal to quantify awareness, while a DOC measure may be based on a second feature of the received signal.

At step 408, an awareness metric derived at step 404 and a DOC measure derived at step 406 (referred to herein as "the derived quantities") may be evaluated. In an embodiment, step 408 may include determining a confidence for one or more of the derived quantities. Certain types of noise and artifact may influence one of these quantities more than another, and such noise may reduce the amount of useful information regarding patient consciousness that may be obtained from the quantity. For example, certain patient movements may distort an awareness metric derived from a PPG signal while having little or no influence on a DOC measure such as a BIS index, while certain types of hardware noise may distort a BIS index calculation while leaving a PPG signal largely unperturbed. Determining a confidence in a quantity at step 408 may involve determining an amount (relative or absolute) of useful information about patient awareness and/or depth of consciousness contained in the quantity. Determining a confidence in a quantity may involve determining an amount of noise affecting the quantity.

Determining a confidence in a quantity such as an awareness metric or a DOC measure, as may be performed at step 408, may involve deriving qualitative or quantitative measurements of the quality of the information contained in the quantity. A confidence may be a single value, or may be a waveform that varies in time. In an embodiment, a confidence in one or more of an awareness metric and a DOC measure may be based on a correlation between the quantities. In an embodiment, a correlation may be based on the Pearson product moment correlation, and may be calculated in accordance with $$\frac{1}{T-1}\sum_{i=1}^{T}\left(\frac{x_i - \bar{x}}{s_x}\right)\left(\frac{y_i - \bar{y}}{s_y}\right), \qquad (1)$$

where T is the number of samples or measurements; $x_i$ and $y_i$ are the ith measurements of the derived quantities x and y, respectively (e.g., an awareness metric and a DOC measure); $\bar{x}$ and $\bar{y}$ are the respective sample means; and $s_x$ and $s_y$ are the respective sample standard deviations. A correlation may be calculated in accordance with any known techniques, including those described in Watson et al., U.S. patent application Ser. No. 12/398,826, filed Mar. 5, 2009, entitled "SYSTEMS AND METHODS FOR MONITORING HEART RATE AND BLOOD PRESSURE CORRELATION," which is incorporated by reference herein in its entirety. A correlation may also be carried out on a transformation of the measurements (e.g., in the Fourier or wavelet domains), or on a filtered or otherwise mathematically manipulated version of the measurements (e.g., removing noisy, outlying or erroneous values prior to performing a correlation calculation).

In an embodiment, a confidence may be determined based on an assessment of an amount or type of noise affecting one or more of an awareness metric and a DOC measure. Assessing an amount of noise may involve detecting a characteristic waveform feature, such as a feature corresponding to the noise signature of a hardware device in the environment (e.g., 60 Hz interference). Assessing an amount of noise may involve detecting an abnormality in features of a waveform, such as those that arise in a PPG or EEG during patient movement. An amount of noise may be assessed by a quantitative or qualitative assessment, which may be used in an inverse or complementary relationship to a confidence determination. Additional noise characterization techniques are described in Addison et al., U.S. patent application Ser. No. 12/497,824, filed Jul. 6, 2009, entitled "SYSTEMS AND METHODS FOR EVALUATING A PHYSIOLOGICAL CONDITION," which is incorporated by reference herein in its entirety.

In an embodiment, an evaluation at step 408 may include a validation of one or more of the derived quantities. A validation may include determining whether or not a derived quantity falls within a range of physiologically relevant values (which may be predefined and stored, for example, in ROM 52 (FIG. 2)). Validation may include a cross-comparison of one or more of the derived quantities with another quantity, such as another derived quantity, a previously-derived quantity or a quantity derived from another signal. A cross-comparison may determine whether the physiological information conveyed by one or more of the derived quantities is reasonable and/or consistent with additional information about a patient.

In an embodiment, step 408 may include evaluating an awareness metric waveform (e.g., awareness metric waveform 1102 (FIG. 7)) to identify an awareness event. Such an embodiment is discussed in detail further below.

At step 410 of FIG. 4, DOC information may be provided. This DOC information may be based at least in part on the evaluation at step 408. In an embodiment, information from the awareness metric derived at step 404 and the DOC measure derived at step 406 may be combined to provide DOC information at step 410. For example, the derived quantities may be combined in a weighted sum to form a combined measure. In an embodiment, one or more of the quantities derived at steps 404 and 406 may be manipulated (e.g., rescaled by a linear or non-linear function) so that the two quantities may be suitably combined by a weighted sum. A combined measure based on a weighted sum of an awareness metric (e.g., as derived from features of a PPG signal) and a DOC measure (e.g., a BIS index) may be output (e.g., via output 314 (FIG. 3)) to a suitable display such as display 28 (FIG. 1) of multi-parameter patient monitor 26 (FIG. 1).

At step 410 of FIG. 4, information from the derived quantities may be combined based at least in part on a confidence or confidences determined at step 408. In an embodiment, the quantities may be combined by performing a weighted summation, where the weighting of a particular quantity depends at least in part on an associated confidence. For example, a combined DOC measure, $x_{total}$, may be calculated in accordance with $$x_{total} = \sum_{i=1}^{N} w_i x_i, \quad (2)$$

where N represents the total number of quantities (e.g., instances of the derived quantities) to be combined, $w_i$ represents the weight associated with quantity i and $x_i$ represents the value of quantity i. The weight $w_i$ may be calculated in any of a number of ways. In an embodiment, the weight $w_i$ is a monotonic transformation of any of the confidences described above with reference to step 408. An awareness metric and a DOC measure may also be combined via any suitable nonlinear combination, which may or may not include weights as described above.

In an embodiment, combining an awareness metric and a DOC measure at step 410 may include a threshold test on one or more of the quantities. A threshold test may determine the degree to which a quantity should be included in a combination. Generally, a threshold test on a value may test any of a number of threshold conditions, including whether the value exceeds a single threshold, whether the value is below a single threshold, or whether the value falls within a specified range or ranges. A threshold test may be fixed, and retrieved by processor 312 (FIG. 3) from ROM 52 (FIG. 2) or RAM 54 (FIG. 2). A threshold test may be dynamic and depend, for example, on previously-derived awareness metrics, previously-derived DOC measures, additional measures of awareness, or any combination thereof. A threshold test may also depend on secondary signal quality indicators, such as an electromagnetic noise measuring device or a signal arising from sensor 318 (FIG. 3) indicating a malfunction or undesirable operating condition. In an embodiment, a quantity may be included in the combination if an associated confidence exceeds a threshold, and may not be included otherwise. In an embodiment, a quantity may be included in the combination with a first weight if an associated confidence exceeds a first threshold, and may be included in the combination with a second, higher weight if the associated confidence exceeds a second, higher threshold. These specific embodiments are illustrative, and appropriate threshold tests may include any number of threshold conditions and resulting implications for the combination of derived quantities.

Step 410 of FIG. 4 may include outputting DOC information. DOC information may be output through a graphical representation, a quantitative representation, a qualitative representation, or combination of representations. DOC information may be output via output 314 (FIG. 3) and may be controlled by processor 312 (FIG. 3). Output 314 may transmit DOC information by any means and through any format useful for informing a patient and/or a care provider of a patient status and may involve recording DOC information to a storage medium. Quantitative or qualitative DOC information provided by output 314 may be displayed on a display (e.g., display 28 (FIG. 1)). A graphical representation may be displayed in one, two, or more dimensions and may be fixed or change with time. A graphical representation may be further enhanced by changes in color, pattern, or any other visual representation. Output 314 may communicate DOC information by performing at least one of the following: presenting a screen on a display; presenting a message on a display; producing a tone or sound; changing a color of a display or a light source; producing a vibration; and sending an electronic message. Output 314 may perform any of these actions in a device close to the patient, or at a mobile or remote monitoring device as described previously. In an embodiment, output 314 produces a continuous tone or beeping whose frequency changes in response to changes in a patient's DOC. In an embodiment, output 314 produces a colored or flashing light which changes in response to changes in a patient's DOC.

As described above, in an embodiment, step 408 of FIG. 4 may include determining a confidence for one or more of the derived quantities. In such an embodiment, one or more of the derived quantities may be provided as DOC information along with the determined confidence at step 410. For example, a DOC measure derived at step 406 (e.g., a BIS index) may be displayed on a patient monitor along with a confidence level indication based at least in part on an awareness metric derived at step 404. A confidence level indication may be a numeric value (e.g., a percentage from 0 to 100 indicating minimal to maximal confidence in a derived quantity) or may be a qualitative indicator (e.g., a green, yellow or red color indicator, each indicating one of three levels of confidence).

In an embodiment, a confidence determined at step 408 may be subject to a threshold test at step 410 to determine how DOC information is to be determined and/or provided. For example, a correlation between an awareness metric derived at step 404 and a DOC measure derived at step 406 may be used to provide a confidence in the awareness metric or the DOC measure. If this confidence is high enough (e.g., if the correlation exceeds a threshold value), monitoring operations may be performed according to a nominal set of parameters. This nominal parameter set may correspond to a "normal" operating state of the patient monitoring system. Such a set of parameters may include displaying one or more of the derived quantities on at least one of display 20 (FIGS. 1 and 2) and display 28 (FIG. 1), storing one or more of the derived quantities (e.g., in RAM 54 (FIG. 2)), using one or more of the derived quantities in other calculations performed by the system, or any combination thereof. Such calculations may include a patient condition estimation routine or a patient status prediction routine.

If it is determined at step 410 of FIG. 4 that the confidence does not pass the threshold test (e.g., the correlation falls below a threshold value), monitoring operations may be performed according to an alternate set of parameters. This alternate parameter set may correspond to a "low confidence" operating state of the patient monitoring system. Such a state may indicate reduced confidence in the amount of information about patient awareness contained in one or more of the derived awareness metric and the derived DOC measure. The corresponding parameter set may include displaying a "low confidence" warning signal via display 20 (FIGS. 1 and 2) or display 28 (FIG. 1), or an audible warning via speaker 22 (FIGS. 1 and 2) or speaker 30 (FIG. 1). In some embodiments, a parameter display color may change as the confidence decreases (e.g., from green to yellow to red). In some embodiments, the range of error or confidence may be indicated numerically or graphically. The parameter set may also include suppressing the display of one or more of the derived quantities, suppressing the storing of one or more of the derived quantities, suppressing the use of one or more of the derived quantities in other calculations performed by the system, or any combination thereof.

In an embodiment, a patient monitoring system may use a confidence determined at step 408 of FIG. 4 to adjust monitoring operations. For example, multi-parameter monitor 26 (FIG. 1) may provide a derived DOC measure on display 28 (FIG. 1). This derived DOC measure may be calculated by processor 312 (FIG. 3) as a running average of measurements made of one or more physiological signals (e.g., a physiological signal received at step 402 of FIG. 4 or any one or more additional physiological signals) over a time window. A confidence determined at step 408 may be used to determine the length of this time window, with lower confidence values suggesting wider time windows and vice versa. Alternately, the length of the time window may be fixed, but each measurement within the window may be weighted within a running average by an associated confidence. In such an embodiment, a low confidence measurement or derived quantity may have relatively less influence on the DOC information displayed by multi-parameter monitor 26 (FIG. 1) than a higher confidence measurement or derived quantity.

As suggested above, in an embodiment, step 408 of FIG. 4 may include generating an electronic awareness event flag representative of an awareness event. An awareness event flag may identify a value or change in a derived awareness metric which indicates a level or change in level of patient awareness (e.g., flagging a microarousal event). In an embodiment, an awareness event flag may be used to "override" a DOC measure nominally made at step 406 or provided at step 410. For example, an increase in cardiac output (e.g., detected by an increase in heart rate and/or a decrease in pulse amplitude of a PPG signal) may indicate that a patient is highly aware and thus an awareness event flag may be generated. Information regarding the awareness event flag may be displayed to a care provider in lieu of or in addition to a DOC measure.

An electronic awareness event flag may be generated, for example, by processor 312 (FIG. 3) and transmitted to output 314 (FIG. 3). Output 314 may represent an indicator device such as displays 20 (FIGS. 1 and 2) and 28 (FIG. 1), speakers 22 (FIGS. 1 and 2) and 30 (FIG. 1), a paper or physical recording device, an electronic memory such as RAM 54 (FIG. 2), or any combination thereof. An electronic awareness event flag generated at step 408 of FIG. 4 may take any suitable form for communication of awareness event information to a device, patient or care provider.

Plot 1104 of FIG. 7 depicts a number of features of awareness metric waveform 1102 that may be used to generate an awareness event flag. An illustrative event flag process will now be discussed with reference to FIG. 7. In an embodiment, an awareness event flag may be generated based at least in part on a comparison between a derived awareness metric and at least one reference value. For example, at time point $t_C$ 1106, a corresponding awareness metric value $A_c$ 1108 may be determined. Awareness metric value $A_c$ 1108 may then be compared against a reference value. In an embodiment, a reference value may be a value derived from past values of awareness metric waveform 1102. These past values may be values arising over a time window or windows. As described above, the term "time window" may be generally used to refer to one or more intervals of time, a number of periods in a signal with periodic features, or a combination thereof. For example, awareness metric value $A_c$ 1108 may be compared against a reference value calculated over a time window of length $T_W$ 1110 located at a time delay $T_D$ 1112 prior to $t_C$ 1106. In an embodiment, the length $T_W$ 1110 may be chosen to roughly correspond to an integer number of heartbeats of a patient. The reference value calculated over a time window may include any of a mean value, a weighted mean value, a median value, a maximum value, a minimum value, a gradient value, a standard deviation value, or any of a number of measures described herein and described in additional detail below. In an embodiment, a reference value may be derived from substantially all past values of awareness metric waveform 1102, and may be based at least in part on any of the above measures. In an embodiment, a reference value may be a fixed value, or may be based on patient-specific information such as age, weight, gender, health status, type of anesthetic or analgesic administered, amount of anesthetic or analgesic administered, past history of consciousness during anesthesia or analgesia administration, duration of unconsciousness, any other relevant criterion, or any combination thereof. Reference values based on past values of an awareness metric waveform may be advantageously applied to physiological signals that vary considerably from patient to patient and across time, and may improve the accuracy of awareness event detectors by making useful assessments of relative awareness. In an embodiment, an awareness metric value or waveform may be provided along with a triggered flag to provide additional information regarding a detected awareness event.

In an embodiment, a comparison between an awareness metric value (e.g., from awareness metric waveform 1102 of FIG. 7) and a reference value may take the form of a threshold test as described above. A threshold test may be fixed, and retrieved by processor 312 (FIG. 3) from ROM 52 (FIG. 2) or RAM 54 (FIG. 2). A threshold test may be dynamic and depend, for example, on past values of a received physiological signal or derived signal (such as awareness metric waveform 1102). A threshold test may also depend on signal quality indicators, such as an indicator arising from an electromagnetic noise measuring device or a signal arising from sensor 318 (FIG. 3) indicating a malfunction or undesirable operating condition. In such an embodiment, an indicator of low signal quality may result in adjusting the parameters of a threshold test to reduce the possibility of false alarm or a missed awareness event.

In an embodiment, thresholds may be set at points above a reference value, below a reference value, substantially equal to a reference value, or any combination thereof. These thresholds may define a range or ranges of values within which the awareness metric value may fall. For example, FIG. 7 illustrates a reference value μ 1114, which is the mean value calculated over the illustrated window of length $T_W$ 1110. Upper threshold $\alpha_U$ 1116 and lower threshold $\alpha_L$ 1118 may be set. Upper and lower thresholds may be located at equal intervals from the reference value, or may be located at unequal intervals. Thresholds may vary in time, and may be based at least in part on awareness metric waveform 1102. In an embodiment, a threshold may be set at a multiple of the standard deviation of the awareness metric waveform over a time window above or below a reference value. In an embodiment, a threshold may be set as a multiple or fraction of the mean of the awareness metric waveform over a time window.

In an embodiment, multiple thresholds may be set. Each of these multiple thresholds may indicate a different level or nature of an awareness event. Each of these multiple thresholds may trigger a corresponding awareness event flag, which may have differing values. A threshold test may include one or more upper thresholds, one or more lower thresholds, or a combination thereof. Thresholds may be set based on any number of factors, including features of the awareness metric waveform, signal quality indicators, and patient-specific information. Factors that may influence the setting of thresholds are discussed in additional detail below.

The results of a threshold test may trigger an awareness event flag. For example, FIG. 7 illustrates an awareness event flag triggered at time $t_E$ 1120 when awareness metric waveform 1102 exceeds upper threshold $\alpha_U$ 1116. The triggering of the awareness event flag is indicated in plot 1122 of FIG. 7 by an event flag value of "1." In an embodiment, generating an awareness event flag may include setting an awareness event flag variable equal to a specified value or values in a memory (e.g., RAM 54 (FIG. 2)). In an embodiment, generating an awareness event flag may include generating a logic signal that may be passed directly to an output. In an embodiment, generating an awareness event flag may include generating a signal to be transmitted which encodes the result of a threshold test in an amplitude, frequency, duty cycle, waveform shape, or other feature of a signal. At time $t_F$ 1124, the value of the awareness event flag is set back to "0," which may indicate the end of an awareness event or a return to a nominal patient state. Resetting the event flag to "0," or performing any adjustment of an event flag or flags, may be triggered by a threshold test or tests as described above. As is discussed in additional detail below, in an embodiment, one or more different flags may be generated to indicate one or more types of awareness events. It will be understood that the triggering of an event flag in response to an awareness metric waveform exceeding an upper threshold, as illustrated in FIG. 7, is simply an example of an awareness event determination process. Many other such processes are within the scope of this disclosure. For example, an awareness event flag may be triggered when an awareness metric waveform decreases below a lower threshold (such as lower threshold $\alpha_L$ 1118), which may indicate a decrease in awareness and signal an awareness event. An awareness event flag may be suitably triggered whenever a significant change in awareness is detected.

The sensitivity and performance of an awareness event detection process may be adjusted by, for example, changing the form and parameters of an awareness event flag threshold test. In an embodiment, the sensitivity and performance of the process illustrated by FIG. 7 and described above may be adjusted by changing one or more of the parameters such as $\alpha_U$ 1116, $\alpha_L$ 1118, $T_W$ 1110, and $T_D$ 1112. Threshold conditions which trigger an awareness event flag may be determined by past measurements of a patient's physiological signals, expected statistical distributions of physiological signals, analytical or theoretical models of physiological function, empirical or observational data of physiological signals of a population, or any combination thereof. In an embodiment, a derived DOC measure (such as a BIS index) may be monitored in conjunction with an awareness metric waveform and may be used to set appropriate thresholds.

In an embodiment, an awareness event flag may be triggered in response to a result of a threshold test on a standard deviation of the awareness metric waveform over a window or windows. A large standard deviation suggests a wide spread of data, which may be indicative of a sudden change in awareness. Any such measure of variability and/or dispersion may also be used, including, for example, a variance, an entropy, and an index of variability.

In an embodiment, a threshold test for triggering a subsequent awareness event flag may be based on current or past values of the awareness event flag. In an embodiment, a Schmitt trigger may be used to trigger and reset an awareness event flag. For example, an awareness event flag may be triggered when an awareness metric waveform is greater than a first deviation from a nominal value, and may not be reset until the awareness metric waveform drops below a value that is less than a second deviation from the nominal value. In an embodiment, a threshold for a second positive event flag may be higher or lower than a threshold for a first positive event flag (and analogously for negative event flags). For example, a first threshold may be set for a first positive event flag to indicate the onset of an awareness event. A second positive event flag, which may indicate a further increase in a patient's awareness, may be triggered when the awareness metric waveform exceeds a second threshold that represents a smaller increase in awareness than was required to trigger the first positive event flag. Such a trigger allows for adjustable sensitivity of the event flags to different ranges of the awareness metric waveform, which may correspond to more or less critical patient awareness conditions.

In an embodiment, a threshold test may include a time component that may be satisfied before an effort event flag is triggered. For example, an awareness metric waveform or derived DOC measure may cross a threshold briefly due to transient artifact, without indicating the onset of a true awareness event. In an embodiment, a threshold may be required to be crossed for a predetermined length of time before triggering a flag. This length of time may depend on the awareness metric waveform, a derived DOC measure, or any other source of patient information relevant to awareness event detection. Such an embodiment may advantageously mitigate against triggering due to transient artifacts of limited time duration.

After or during the providing of DOC information at step 410 of FIG. 4, the illustrative steps of flow chart 400 may begin again. Either a new signal may be received, or the physiological information determination may continue on another portion of the received signal(s). In an embodiment, processor 312 (FIG. 3) may continuously or periodically perform steps 402-410 and update the DOC information. The steps may repeat indefinitely, until there is a command to stop the monitoring and/or until some detected event occurs that is designated to halt the monitoring process. For example, it may be desirable to halt a monitoring process when a detected noise has become too great, or when a patient has undergone a change in condition that can no longer be sufficiently well-monitored in a current configuration. In an embodiment, processor 312 (FIG. 3) may perform steps 402-410 at a prompt from a care provider via user inputs 56 (FIG. 2). In an embodiment, processor 312 (FIG. 3) may perform steps 402-410 at intervals that change according to patient status. For example, steps 402-410 may be performed more often when a patient is undergoing rapid changes in physiological condition, and may be performed less often as a patient's condition stabilizes.

Several of the steps of flow chart 400 may be aided by the use of a predictive model. For example, a predictive model may be employed in at least one of step 404 for deriving an awareness metric, step 406 for deriving a DOC measure, step 408 for evaluating a derived quantity, and step 410 for providing DOC information. In an embodiment, a predictive computational model may detect and characterize a feature or features of a physiological received at step 402 indicative of a patient's awareness. In an embodiment, a predictive computational model may estimate a patient's current awareness level (or depth of consciousness) and prognosis as part of the DOC information provided at step 410. In an embodiment, a predictive computational model may learn to identify features of a physiological signal (such as a PPG signal) which correlate or anti-correlate with a DOC measure (such as a BIS index). Features identified by such a model may then be used in an awareness metric (e.g., as derived at step 404). A predictive computational model executed, for example, by processor 312 (FIG. 3), may be based in part on at least one of the following data sources: the signal received at step 402 of FIG. 4 (e.g., input signal 316 (FIG. 3)); additional physiological signals; patient characteristics; historical data of the patient or other patients; and computational or statistical models of physiological processes such as anesthetic or analgesic response models. Processor 312 (FIG. 3) may retrieve any of these data sources from memory such as ROM 52 (FIG. 2) or RAM 54 (FIG. 2), from an external memory device, or from a remote device. The structure of a predictive computational model may, for example, be based on any of the following models: a neural network, a Bayesian classifier, and a clustering algorithm. In an embodiment, processor 312 (FIG. 3) may develop a predictive neural network for noise assessment based at least in part on historical data from the given patient and/or other patients. In some embodiments, processor 312 may implement the predictive computational model as a hypothesis test. Processor 312 may continually refine or augment the predictive computational model as new patient data and/or physiological signals are received. The predictive model may also be refined based on feedback from the patient or care provider received through the user inputs 56 (FIG. 2). For example, a patient or care provider may supply feedback to system 10 (FIGS. 1 and 2) regarding a patient's awareness level based on observed characteristics, which may then be used by system 10 to improve the performance of its awareness monitoring functionality. Other predictive frameworks may include rule-based systems and adaptive rule-based systems such as propositional logic, predicate calculus, modal logic, non-monotonic logic and fuzzy logic.

It will also be understood that the methods disclosed herein may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure.

What is claimed is:

1. A physiological monitoring method comprising:
   receiving a photoplethysmograph signal;
   deriving an awareness metric based at least in part on the photoplethysmograph signal;
   deriving at least one depth of consciousness measure;
   evaluating the awareness metric and the depth of consciousness measure; and
   providing depth of consciousness information based at least in part on the evaluation, wherein the providing comprises:
      determining first and second non-zero weights based at least in part on the evaluation; and
      determining a weighted sum of the awareness metric and the depth of consciousness measure based at least in part on the first and second non-zero weights.

2. The method of claim 1 wherein the awareness metric is at least based in part on a change in morphology of the photoplethysmograph signal.

3. The method of claim 1 wherein the awareness metric indicates a change in vasotone.

4. The method of claim 1, wherein the depth of consciousness measure is based at least in part on an electrophysiological signal.

5. The method of claim 1 wherein the depth of consciousness measure is a bispectral index value.

6. The method of claim 1 wherein evaluating the awareness metric and the depth of consciousness measure comprises determining a confidence for at least one of the awareness metric and the depth of consciousness measure.

7. The method of claim 1 wherein evaluating the awareness metric and the depth of consciousness measure comprises calculating a correlation of the awareness metric and the depth of consciousness measure.

8. The method of claim 1 wherein providing depth of consciousness information comprises providing the depth of consciousness measure and an indicator of a confidence of the depth of consciousness measure.

9. The method of claim 1, wherein evaluating the awareness metric and the depth of consciousness measure comprises performing a threshold test to determine the degree to which the awareness metric and the depth of consciousness measure are to be included in a combination.

10. The method of claim 9, wherein determining the first and second non-zero weights based at least in part on the evaluation comprises determining the first and second non-zero weights based at least in part on the threshold test.

11. A physiological monitoring system comprising:
   a signal input configured to receive a photoplethysmograph signal of a subject from a sensing device;
   one or more processing devices in communication with the signal input and configured to:
      derive an awareness metric based at least in part on the photoplethysmograph signal;
      derive at least one depth of consciousness measure;
      evaluate the awareness metric and the depth of consciousness measure;
      provide depth of consciousness information based at least in part on the evaluation, wherein the providing comprises:
         determining first and second non-zero weights based at least in part on the evaluation; and
         determining a weighted sum of the awareness metric and the depth of consciousness measure based at least in part on the first and second non-zero weights.

12. The system of claim 11 wherein the awareness metric is at least based in part on a change in morphology of the photoplethysmograph signal.

13. The system of claim 11 wherein the awareness metric indicates a change in vasotone.

14. The system of claim 11, wherein the depth of consciousness measure is based at least in part on an electrophysiological signal.

15. The system of claim 11 wherein the depth of consciousness measure is a bispectral index value.

16. The system of claim 11 wherein evaluating the awareness metric and the depth of consciousness measure comprises determining a confidence for at least one of the awareness metric and the depth of consciousness measure.

17. The system of claim 11 wherein evaluating the awareness metric and the depth of consciousness measure comprises calculating a correlation of the awareness metric and the depth of consciousness measure.

18. The system of claim 11 wherein providing depth of consciousness information comprises providing the depth of consciousness measure and an indicator of a confidence of the depth of consciousness measure.

19. The system of claim 11, wherein the one or more processing devices are configured to evaluate the awareness metric and the depth of consciousness measure by performing a threshold test to determine the degree to which the awareness metric and the depth of consciousness measure are to be included in a combination.

20. The system of claim 19, wherein the first and second non-zero weights are determined based at least in part on the threshold test.

* * * * *